(12) United States Patent
Eaves

(10) Patent No.: US 11,109,826 B2
(45) Date of Patent: Sep. 7, 2021

(54) FLUOROSCOPY SYSTEM WITH MOVABLE IMAGING HEAD/X-RAY DETECTOR

(71) Applicant: Onyx Technical Consulting, LLC, Scottsdale, AZ (US)

(72) Inventor: Christopher Eaves, Scottsdale, AZ (US)

(73) Assignee: Onyx Technical Consulting, LLC, Scottsdale, AZ (US)

( * ) Notice: Subject to any disclaimer, the term of this patent is extended or adjusted under 35 U.S.C. 154(b) by 0 days.

(21) Appl. No.: 16/719,840

(22) Filed: Dec. 18, 2019

(65) Prior Publication Data

US 2020/0196967 A1 Jun. 25, 2020

Related U.S. Application Data

(60) Provisional application No. 62/782,268, filed on Dec. 19, 2018.

(51) Int. Cl.
*A61B 6/00* (2006.01)

(52) U.S. Cl.
CPC .......... *A61B 6/4441* (2013.01); *A61B 6/4452* (2013.01); *A61B 6/487* (2013.01)

(58) Field of Classification Search
CPC ...... A61B 6/4441; A61B 6/487; A61B 6/4452
See application file for complete search history.

(56) References Cited

U.S. PATENT DOCUMENTS

| | | | |
|---|---|---|---|
| 4,805,202 A * | 2/1989 | Deucher | A61B 6/00 378/195 |
| 4,856,036 A | 8/1989 | Malcolm et al. | |
| 7,810,996 B1 | 10/2010 | Giphart et al. | |
| 9,161,727 B2 | 10/2015 | Jenkins et al. | |
| 9,872,659 B2 | 1/2018 | Jenkins et al. | |
| 10,271,807 B2 | 4/2019 | Jenkins et al. | |
| 10,285,660 B2 * | 5/2019 | Zaiki | A61B 6/4429 |
| 10,687,771 B2 * | 6/2020 | Uehara | A61B 6/4441 |

(Continued)

FOREIGN PATENT DOCUMENTS

WO 2018/232037 A 12/2018

OTHER PUBLICATIONS

Machine Translation of Kim (KR 10-457099 B1), 2014.*

(Continued)

*Primary Examiner* — David P Porta
*Assistant Examiner* — Djura Malevic
(74) *Attorney, Agent, or Firm* — Perkins Coie LLP

(57) ABSTRACT

A fluoroscope assembly having a contoured support arm with opposing first and second end portions, an adjustment element coupled to the first end portion or the second end portion, and an imaging head or an X-ray detector coupled to the adjustment element. The adjustment element is movable to adjust a position of the imaging head or the X-ray detector relative to the first and second end portions. The X-ray detector is coupled to the second end portion of the support arm. The adjustment element is configured to allow the imaging head or the X-ray detector to be moved between an aligned position, with the imaging head aligned with the X-ray detector for generating an X-ray image, and a misaligned position wherein the imaging head and the X-ray detector are misaligned and not in a suitable position to obtain an X-ray image.

17 Claims, 17 Drawing Sheets

(56) References Cited

U.S. PATENT DOCUMENTS

| | | |
|---|---|---|
| 2005/0002489 A1 | 1/2005 | Scheuering |
| 2006/0269044 A1 | 11/2006 | Fehre et al. |
| 2007/0140429 A1 | 6/2007 | Hoheisel |
| 2007/0237309 A1 | 10/2007 | Marinelli et al. |
| 2012/0148031 A1 | 6/2012 | Eaves |
| 2013/0089183 A1* | 4/2013 | Sura .................. A61B 6/467 378/98.2 |
| 2013/0243153 A1 | 9/2013 | Sra |
| 2014/0192962 A1 | 7/2014 | Eaves |
| 2015/0342548 A1* | 12/2015 | Zaiki .................. A61B 6/46 378/41 |
| 2016/0174915 A1 | 6/2016 | ODea |
| 2019/0175128 A1 | 6/2019 | Eaves et al. |

OTHER PUBLICATIONS

USPTO, International Search Report and Written Opinion for International Patent Application No. PCT/US2018/037409, dated Sep. 13, 2018. 8 pages.

USPTO, International Preliminary Report on Patentability (Chapter II) for International Patent Application No. PCT/US2018/037409, dated Sep. 6, 2019. 14 pages.

\* cited by examiner

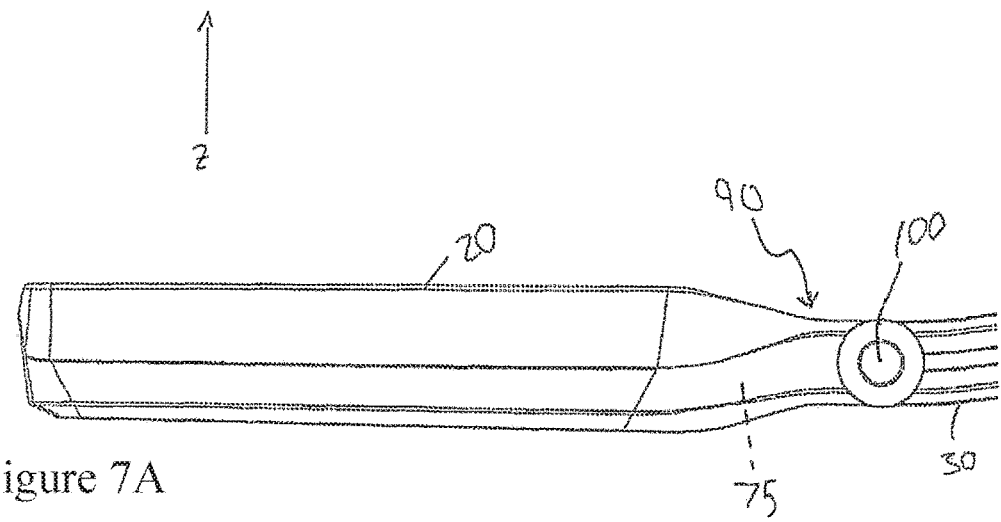
Figure 7A
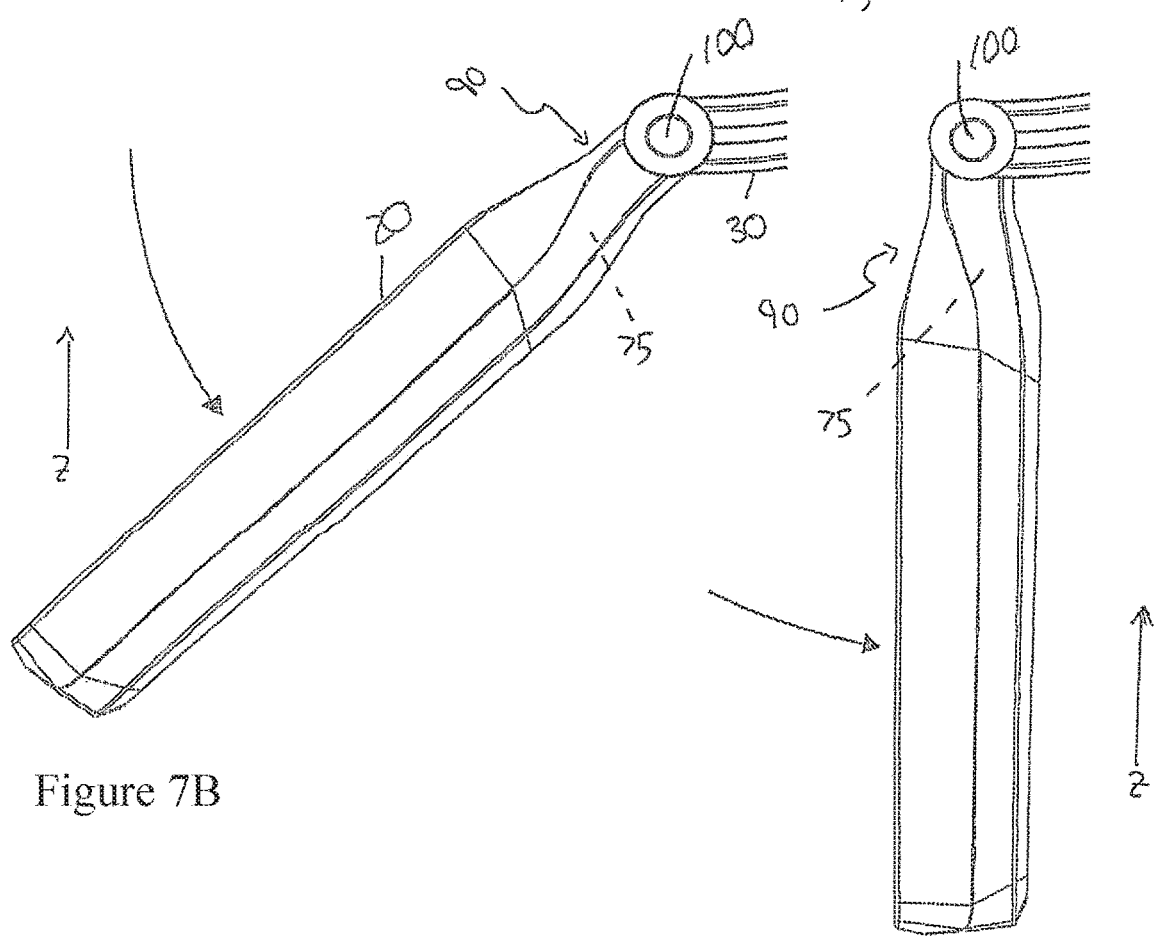
Figure 7B
Figure 7C

FLUOROSCOPY SYSTEM WITH MOVABLE IMAGING HEAD/X-RAY DETECTOR

CROSS-REFERENCE TO RELATED APPLICATIONS

The present application claims the benefit of U.S. Provisional Patent Application No. 62/782,268, filed Dec. 19, 2018, and titled "FLUOROSCOPY SYSTEM WITH MOVABLE IMAGING HEAD/X-RAY DETECTOR," the disclosure of which is incorporated herein by reference in its entirety.

TECHNICAL FIELD

The disclosed technology relates to medical imaging systems and in particular to C-arm fluoroscopy systems.

BACKGROUND

Fluoroscopy systems are used to obtain still or moving images of body tissues using X-rays. In a typical fluoroscope system, a physician or X-ray technician places an area of a patient to be imaged in between an imaging head and an X-ray detector plate. A physician may use a fluoroscope system to visualize the internal structure and organs, hard and soft tissues, blood flow analysis, cardiovascular processes, urological function, and many other aspects of human anatomy. One of the primary advantages presented by using fluoroscopy in a medical capacity rests in being able to observe human internal structures in real-time without the necessity to open the body for a direct or invasive procedure.

SUMMARY

In conventional fluoroscope designs, the components suspended at the end of the gantry (generator/imaging head and image receptor/detector) are rigidly affixed or provide only limited mobility. In certain surgical and clinical scenarios, however, it would be advantageous to be able to move one or both of the components at the end of the gantry to allow a larger working space without moving the entire device from the desired position. This would be first advantageous because the device stays aligned to the desired anatomical target, other than the component being moved temporarily to create working space. Secondarily it would reduce sterile field concerns that arise when the device is moved in and out of the sterile barrier.

To address these needs, the disclosed technology relates to Applicant's fluoroscope having dynamic adjustment elements on each end connecting the imaging head and image detector (e.g., an X-ray detector) to a shaped supporting structure, providing each imaging element with the freedom to move substantially into and out of alignment with each other.

In one embodiment of the present technology, a fluoroscope assembly has a contoured support arm with opposing first and second end portions, an adjustment element coupled to the first end portion, and an imaging head coupled to the adjustment element. The adjustment element is movable to adjust a position of the imaging head relative to the first and second end portions. An X-ray detector is coupled to the second end portion, and the adjustment element is configured to allow the imaging head to be moved between an aligned position, with the imaging head aligned with the X-ray detector for generating an X-ray image, and a misaligned position wherein the imaging head is not substantially aligned with the X-ray detector.

The adjustment element can have a first hinging mechanism that comprises an arm portion, a first hinge coupling the arm portion to the first end portion of the support arm and allowing the imaging head to be moved about the first hinge toward or away from the X-ray detector, and a second hinge coupling the arm portion to the imaging head and allowing the imaging head to be rotated about the second hinge toward or away from the X-ray detector. Movement about the second hinge is substantially independent from movement about the first hinge. The adjustment element can have a hinging mechanism that allows the imaging head to be rotated on a yaw axis along a plane substantially parallel to the X-ray detector. The adjustment element can have a track attached to the imaging head, and a mounting element adjoining the curved track to the support arm. The track and mounting element are configured to allow the imaging head to rotate about a center axis of the imaging head. The adjustment element can have first and second hinging mechanisms. The first hinge mechanism is coupled to the support arm and configured to allow the imaging head to be rotated on a yaw axis for movement in a first plane toward or away from the X-ray detector. The second hinge mechanism has an arm portion, a first hinge connecting the arm portion to the first hinging mechanism and allowing the imaging head to be raised or lowered with respect to the X-ray detector, and an independently addressable second hinge coupled to the arm portion and allowing the imaging head to be rotated in a second plane orthogonal to the first plane for movement away from or towards the X-ray detector. A mounting element can be coupled to the imaging head, and a shaped track is attached to an outside wall of the imaging head and configured to engage with the mounting element. The track and mounting element are configured to allow the imaging head to rotate about a center axis of the imaging head.

The fluoroscope assembly can have a switch with an unlocked state and a locked state, wherein the switch is configured to prevent power to the imaging head when in the locked state. At least one sensor detects a mis-aligned status when the imaging head is not substantially aligned with the X-ray detector and sends a communication of the mis-aligned status. A controlling computer system houses a processor and one or more computer-readable storage mediums for storing computer-executable instructions configured to cause the processor to receive the communication, and move the switch into the locked state.

In another embodiment, a fluoroscope assembly comprises a shaped support arm having a first distal end portion and a second distal end portion, an adjustment element operably connected to the first distal end portion, and an imaging head operably connected to the adjustment element. An X-ray detector is operably connected to the second distal end portion. The adjustment element is configured to allow the imaging head to be moved such that the imaging head is not substantially aligned with the X-ray detector. The adjustment element can have a vertical hinge mechanism with an arm portion, a first hinge connecting the arm portion to the support arm and allowing the imaging head to be raised or lowered with respect to the X-ray detector, and an independently addressable second hinge connecting the arm portion to the imaging head and allowing the imaging head to be rotated away from or towards the X-ray detector. The adjustment element can have a horizontal hinge configured to allow the imaging head to be rotated on a yaw axis away from the X-ray detector.

In another embodiment a fluoroscope assembly comprises a support arm having a first distal end portion and a second distal end portion, a first adjustment element coupled to the first distal end portion, and an imaging head movably coupled to the first adjustment element. A second adjustment element is coupled to the second distal end, and an X-ray detector is movably coupled to the second adjustment element. The first adjustment element is configured to allow the imaging head to be moved relative to the support arm between a first aligned position with the imaging head in alignment with the X-ray detector for generating X-ray images, and a first misaligned position with the imaging head out of alignment with the X-ray detector not suitable for generating X-ray images. The second adjustment element is configured to allow the X-ray detector to be moved relative to the support arm between a second aligned position with the X-ray detector in alignment with the imaging head for generating X-ray images, and a second misaligned position with the X-ray detector out of alignment with the imaging head not suitable for generating X-ray images.

The first adjustment element can have a horizontal hinge connected to the support arm and configured to allow the imaging head to be rotated on a yaw axis away from alignment with the X-ray detector. A vertical hinge mechanism has an arm portion, and a first hinge connecting arm portion to the horizontal hinge allowing the imaging head to be raised or lowered with respect to the X-ray detector. An independently addressable second hinge is connected to the arm portion allowing the imaging head to be rotated away from or towards the X-ray detector. A curved track is attached to an outside wall of the imaging head and configured to engage with a mounting element, wherein the curved track and mounting element are configured to allow the imaging head to rotate about a center axis of the imaging head. The second adjustment element can comprise a horizontal hinge connected to the support arm and configured to allow the X-ray detector to be rotated on a yaw axis away from alignment with the imaging head. A vertical hinge can allow the X-ray detector to be rotated away from or towards the imaging head. A curved track can be attached to an outside wall of the X-ray detector and a mounting element adjoining the track to the vertical hinge, wherein the curved track and mounting element are configured to allow the X-ray detector to rotate about a center axis of the X-ray detector.

In another embodiment, the imaging head is connected to the support element with an adjustment element comprised of a first hinge mechanism with first and second hinges coupled to the imaging head and configured to allow the imaging head to be raised or lowered with respect to the X-ray detector and rotate away from or towards the X-ray detector. A second horizontal hinge element is coupled to the imaging head and configured to allow the imaging head to be rotated on a yaw axis. A curved track extends around the outside of the imaging element and is connected to the first hinge mechanism via a mounting element to allow the imaging head to rotate about a center axis of the imaging head.

In yet another embodiment, the X-ray detector is connected to the support element with an adjustment element comprising a second hinge mechanism connected to the support arm and configured to allow the X-ray detector to be rotated on a yaw axis away from the alignment with imaging head. A vertical hinge is coupled to the X-ray detector and is configured to allow the X-ray detector to be rotated away from or towards the imaging head. A track is attached to the X-ray detector, and the vertical hinge engages the track to allow the X-ray detector to rotate about a center axis of the X-ray detector.

In various other embodiments, the imaging head and/or X-ray detector are only moveable according to a subset of one or more of the aforementioned degrees of freedom. For example, the imaging head may be static while the X-ray detector is attached to a horizontal hinge allowing the X-ray detector to move along a yaw axis, vice versa, or both components may be afforded with only the ability to move along a yaw axis.

In some embodiments, the fluoroscope also has sensors configured to communicate a signal if the imaging head and X-ray detector are not aligned. That signal can be received by a processor, executing computer-executable instructions to either disallow power to the imaging head until the imaging components are realigned or communicate the misalignment to a fluoroscope operator. For example, a message notifying the misalignment can be relayed via a display, such as a warning light, LED (light emitting diode) screen, LCD (liquid crystal display) screen, or other user interface in communication with the processor. The inclusion of sensors is expected to reduce the amount of unintended exposure to X-ray beams made possible by the mobility of the imaging components.

Other embodiments can be directed to a system with an imaging head and/or an X-ray imaging detector that can be moved out of a position that is used for imaging in order to give a physician or X-ray technician more room to position the subject or to maneuver an instrument with respect to the subject. In some embodiments, an imaging head is secured to a C-rail with a hinge mechanism that allows the imaging head to be tilted up and down or moved sideways (left or right) with respect to an X-ray detector. The imaging head can be secured to the C-rail with a hinge that allows the imaging head to rotate left or right. The imaging head can be secured to the C-rail with a curved track that allows the imaging head to rotate left and right about a center axis.

In some embodiments, the X-ray detector is mounted to the C-rail with hinge that allows the X-ray detector to rotate up/down or left/right.

BRIEF DESCRIPTION OF THE DRAWINGS

FIGS. 7A-7C illustrate an embodiment of an X-ray detector mounted to the C-arm with a hinge to allow the detector to be tilted up and down in accordance with the disclosed technology.

DETAILED DESCRIPTION

Various examples or embodiments of the fluoroscope system in accordance with Applicant's technology is described below in further detail. However, some well-known structures or functions may not be shown or described in detail below so as to avoid unnecessarily obscuring the relevant description. Further, for purposes of simplicity of discussion, the fluoroscope system will be described herein with reference to vertical and horizontal, raise and lower, upwards and downwards, left and right, a yaw axis, and/or a central axis relative to the spatial orientation of the embodiment(s) shown in the figures. It is to be understood that the C-arm fluoroscope system, however, can be moved to and used in different spatial orientations without changing the structure of the system.

As indicated above, there are often instances where a physician or an X-ray technician needs to position a portion of a subject to be imaged (human or animal) between an imaging head and an X-ray detector of a fluoroscope. If the subject is large, it may be difficult to place the tissue to be imaged at the correct location with the imaging head or X-ray detector in a fixed position. While many C-arm fluoroscopy systems allow the imaging head and X-ray detector to be rotated as a pair around a single center point, they do not allow the imaging head or X-ray detector to be individually moved for ease of positioning the subject, to provide better access with a surgical tool, to provide better access for otherwise addressing the subject, etc.

The disclosed technology relates to a fluoroscopy imaging system where one or both of the imaging head and an X-ray detector can be moved with respect to each other and with respect to a supporting C-arm.

Figure 1A:
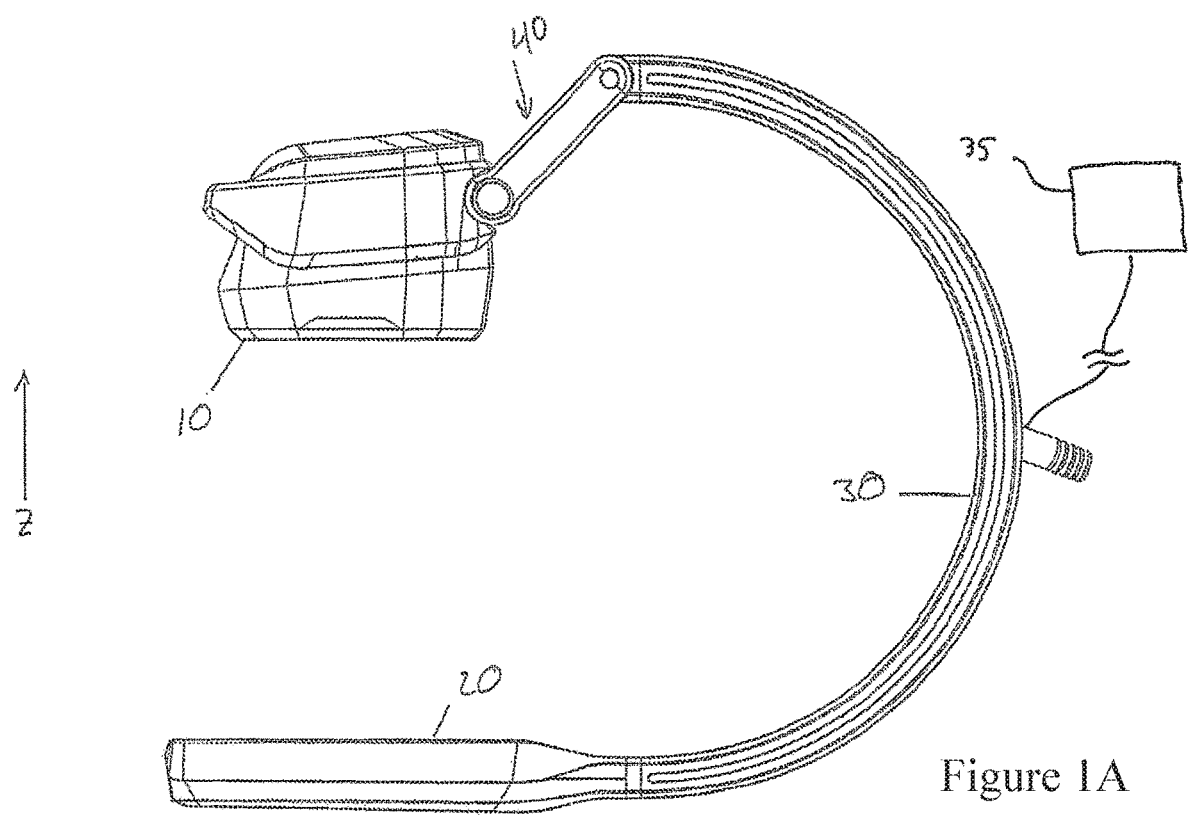
FIGS. 1A and 1B illustrate a C-arm fluoroscope imaging system including an imaging head and an X-ray detector in accordance with at least one embodiment of the present technology.
Figure 1B:
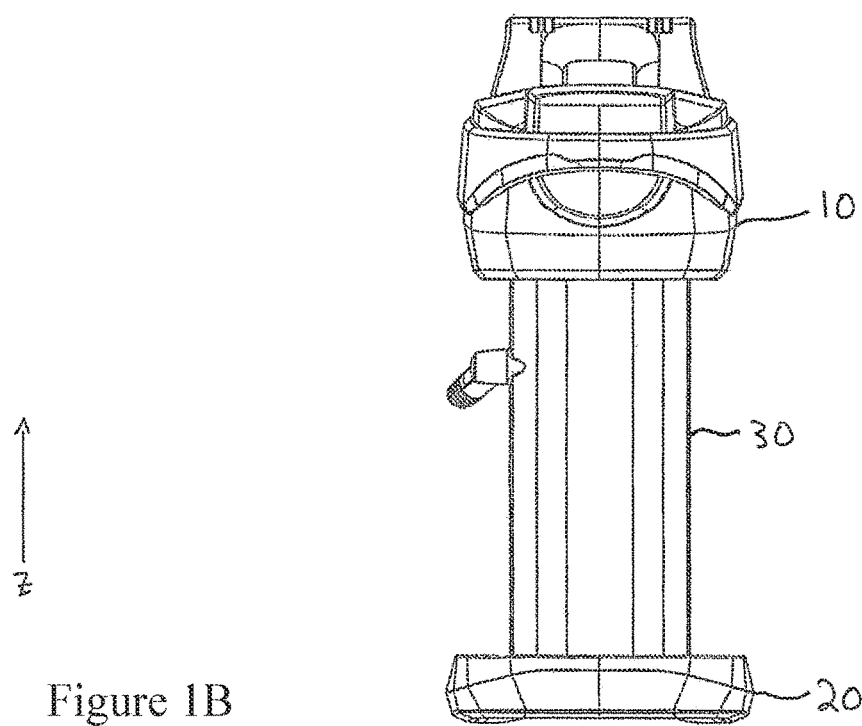

FIGS. 1A and 1B show a C-arm fluoroscopy imaging system including an imaging head 10 and X-ray detector 20 that are mounted to opposite distal ends of a supporting C-arm 30. Further, the fluoroscopy imaging system includes a controlling computer system 35 in communication with the rest of the fluoroscopy imaging system. As will be appreciated by those skilled in the art, the C-arm is generally mounted to a supporting structure (not shown) that allows the C-arm to rotate about a single center point so that the fluoroscopy system can image in the vertical position, in the horizontal position, or any position in between. Unlike conventional fluoroscopy imaging systems, the imaging head 10 (which includes an X-ray source) is mounted to the C-arm 30 with a hinge mechanism, which may be referred to as a vertical hinge mechanism 40, that allows the imaging head 10 to be raised and lowered with respect to X-ray detector 20. Further descriptions of one embodiment of the vertical hinge mechanism are set forth in PCT Patent Application No. PCT/US18/37409 and U.S. patent application Ser. Nos. 16/219,822 and 62/519,707, which are herein incorporated by reference in their entireties.

Figure 2A:
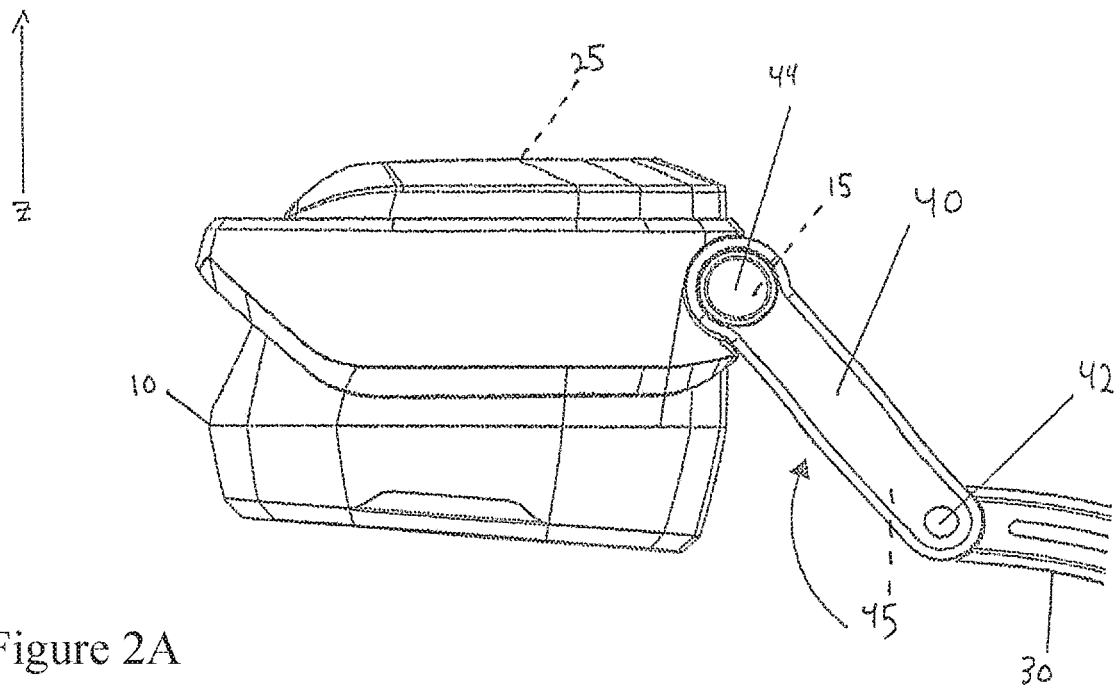
FIGS. 2A-2E illustrate the fluoroscope imaging system of FIGS. 1A and 1B with a vertical hinge mechanism that allows the imaging head to be tilted up and down with respect to the supporting C-arm in accordance with the disclosed technology.
Figure 2B:
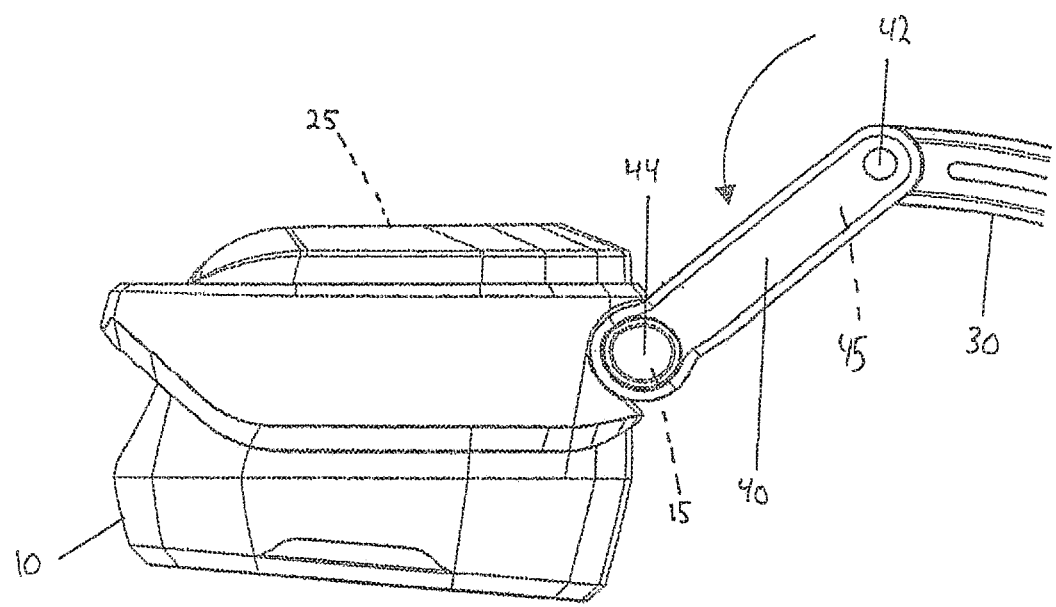

As shown in FIGS. 2A and 2B, the vertical hinge mechanism 40 allows the imaging head 10 to be raised and lowered with respect to the X-ray detector 20 via a first joint 42 (shown in FIGS. 2A and 2B by movement along the Z-axis). Suitable vertical hinge mechanisms include 4-bar linkage mechanisms that keep the X-ray source, i.e., the imaging head 10, perpendicular to and aligned with the X-ray detector 20 as the imaging head is raised and lowered.

Figure 2C:
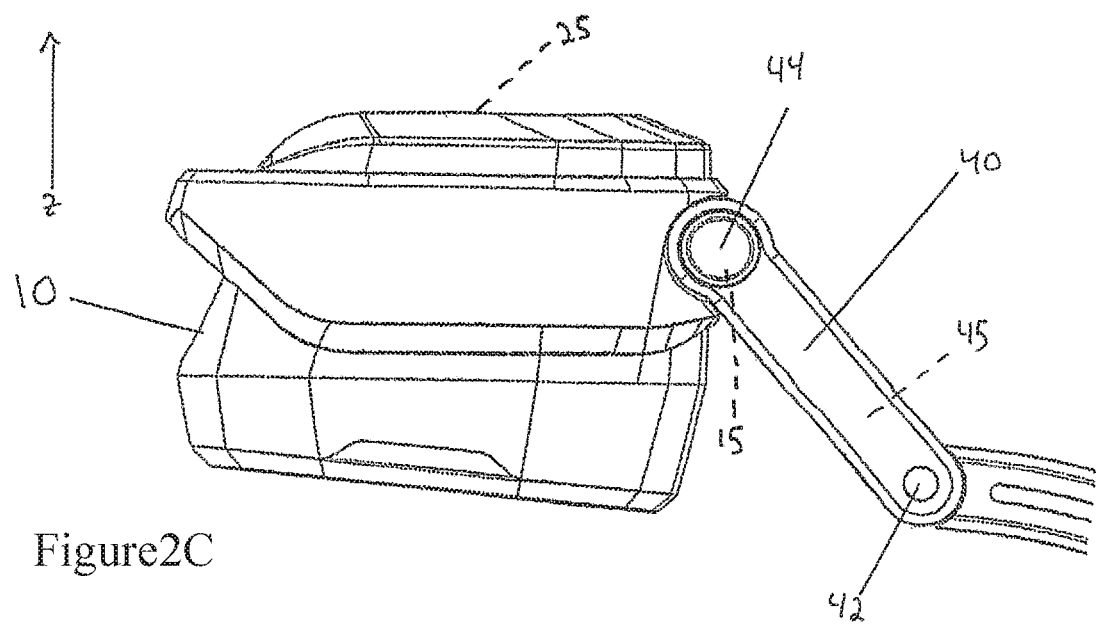
Figure 2D:
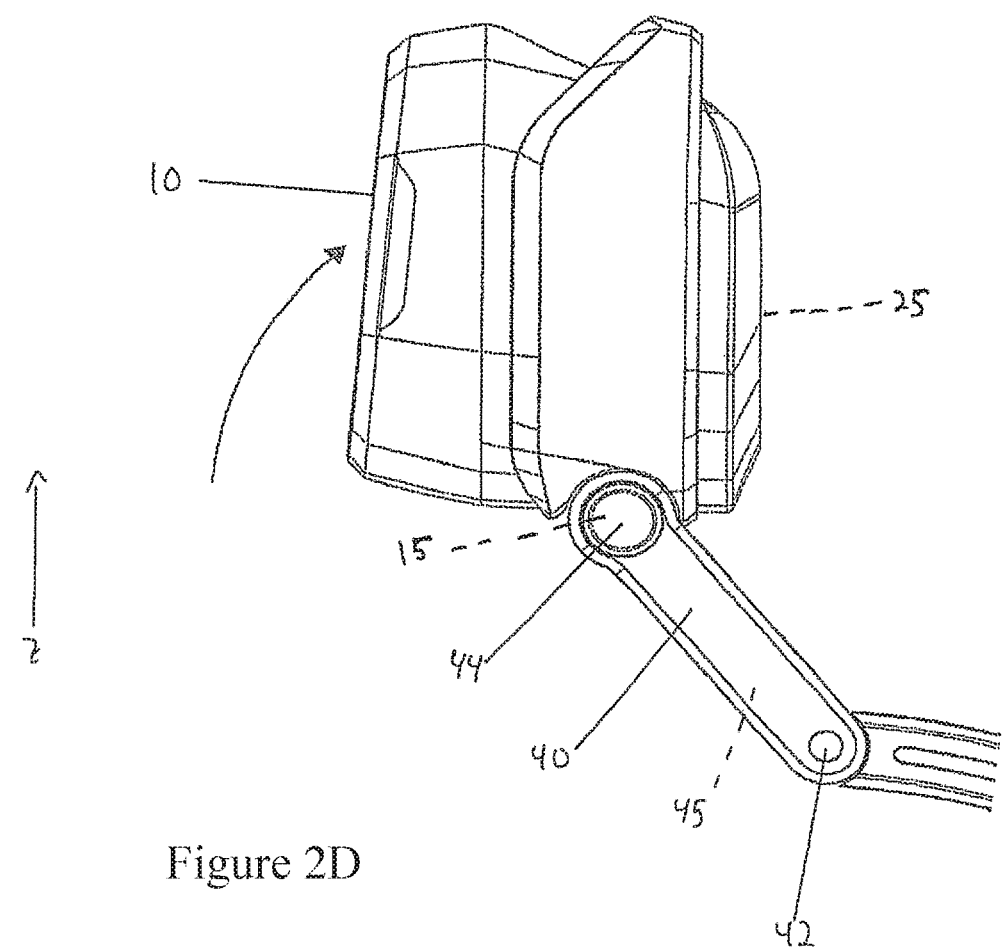
Figure 2E:
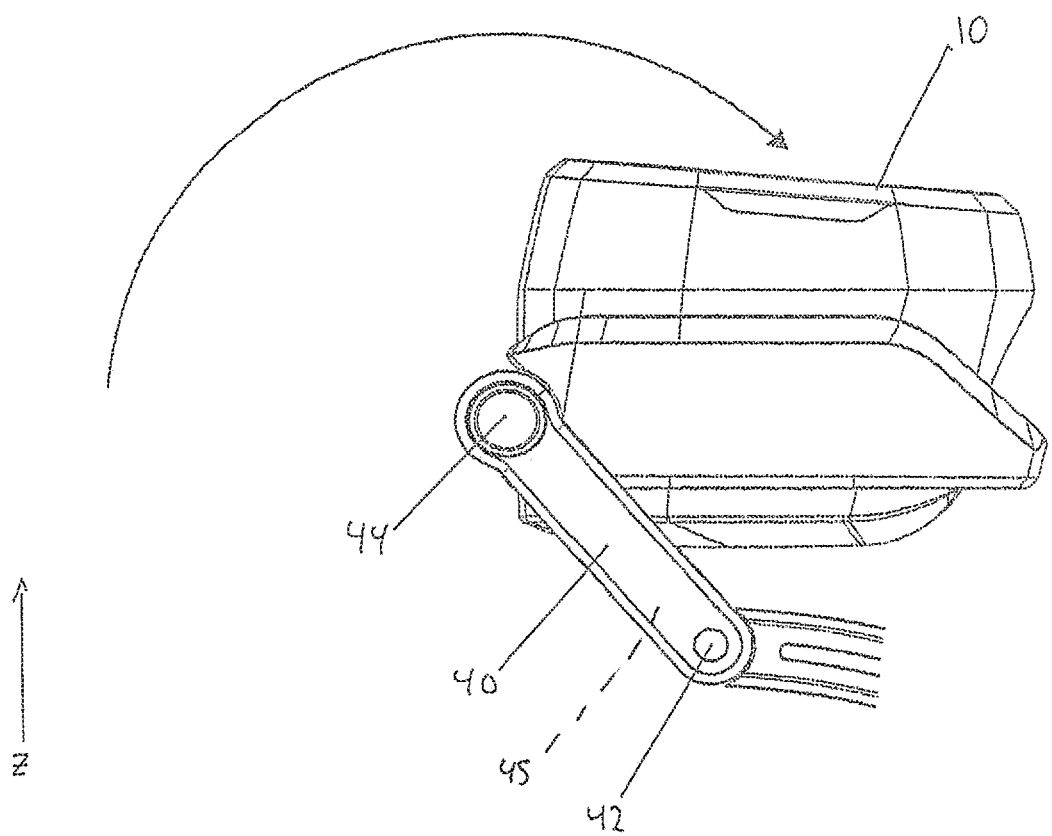
Figure 3A:
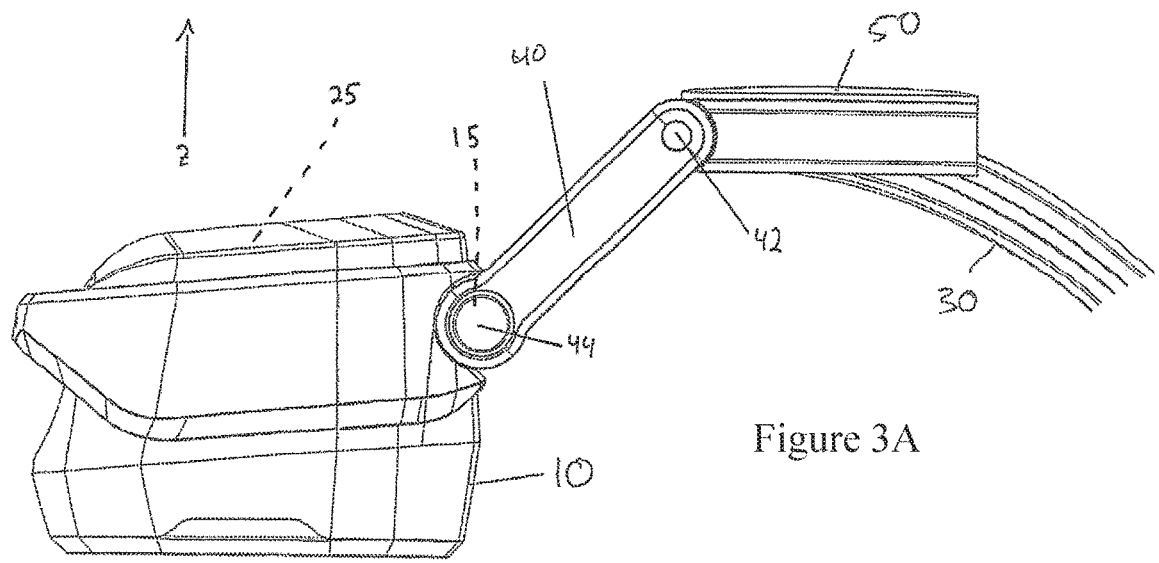
FIGS. 3A-3F illustrate an embodiment of the C-arm fluoroscope system, with a vertical hinge mechanism that allows the imaging head to be rotated left/right with respect to the supporting C-arm in accordance with the disclosed technology.
Figure 3B:
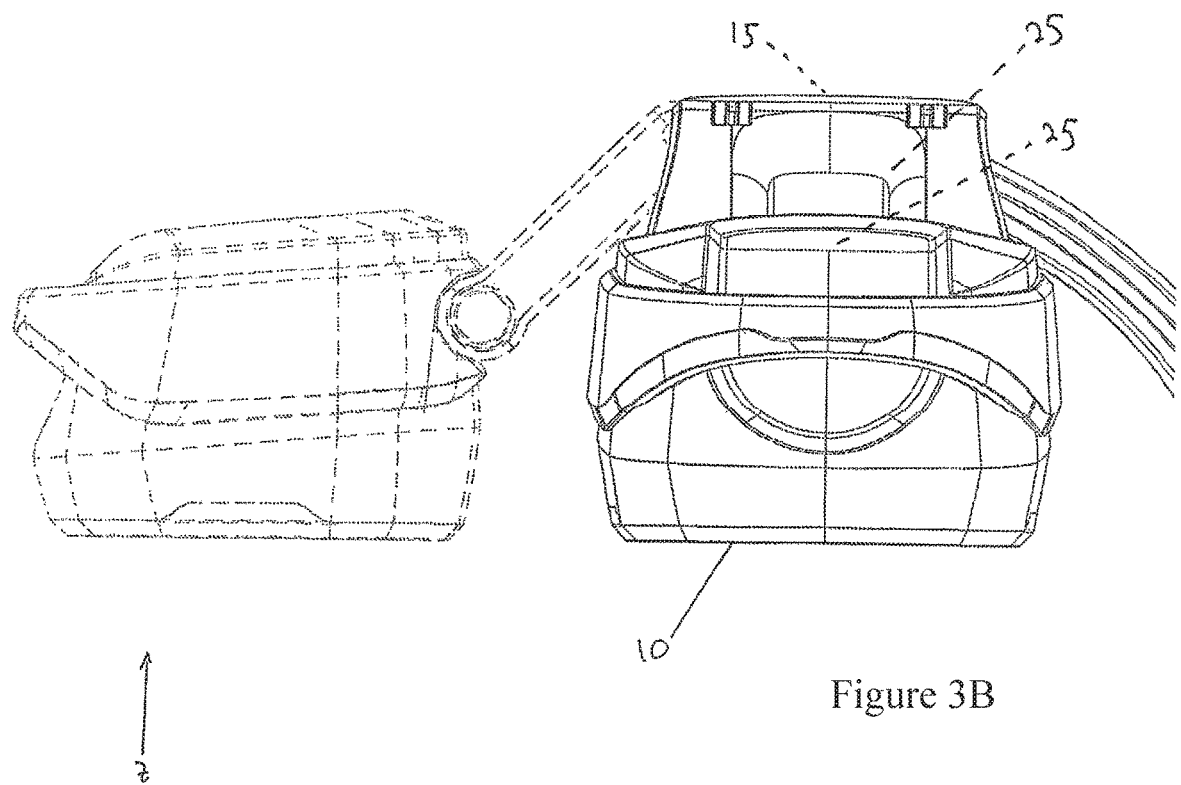
Figure 3C:
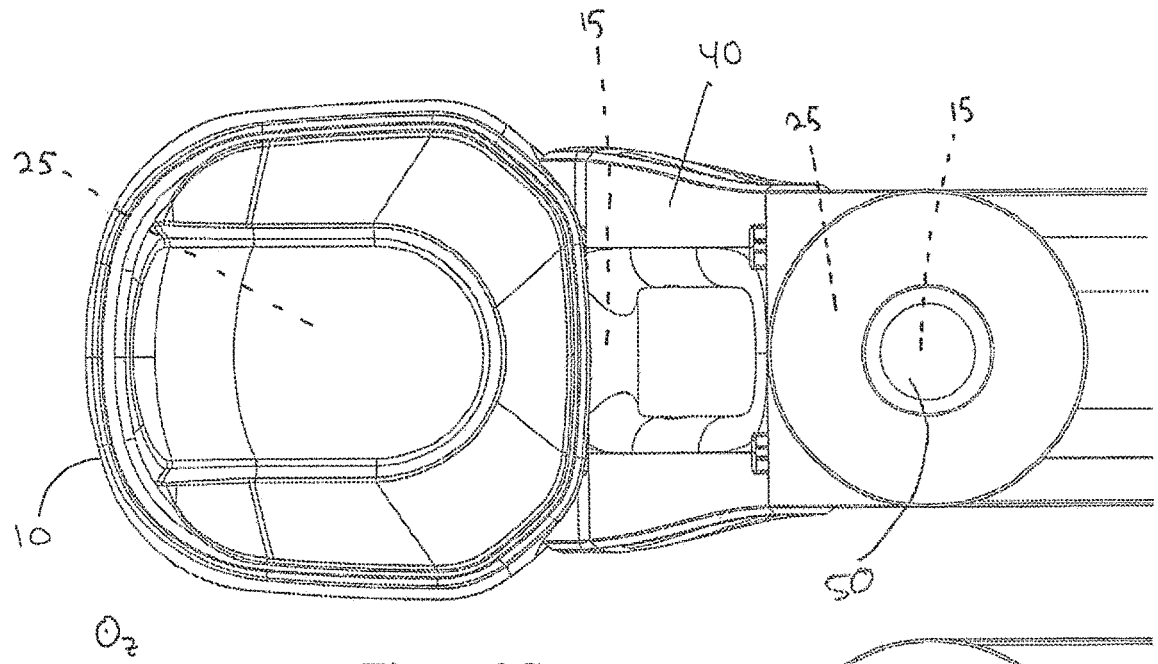
Figure 3D:
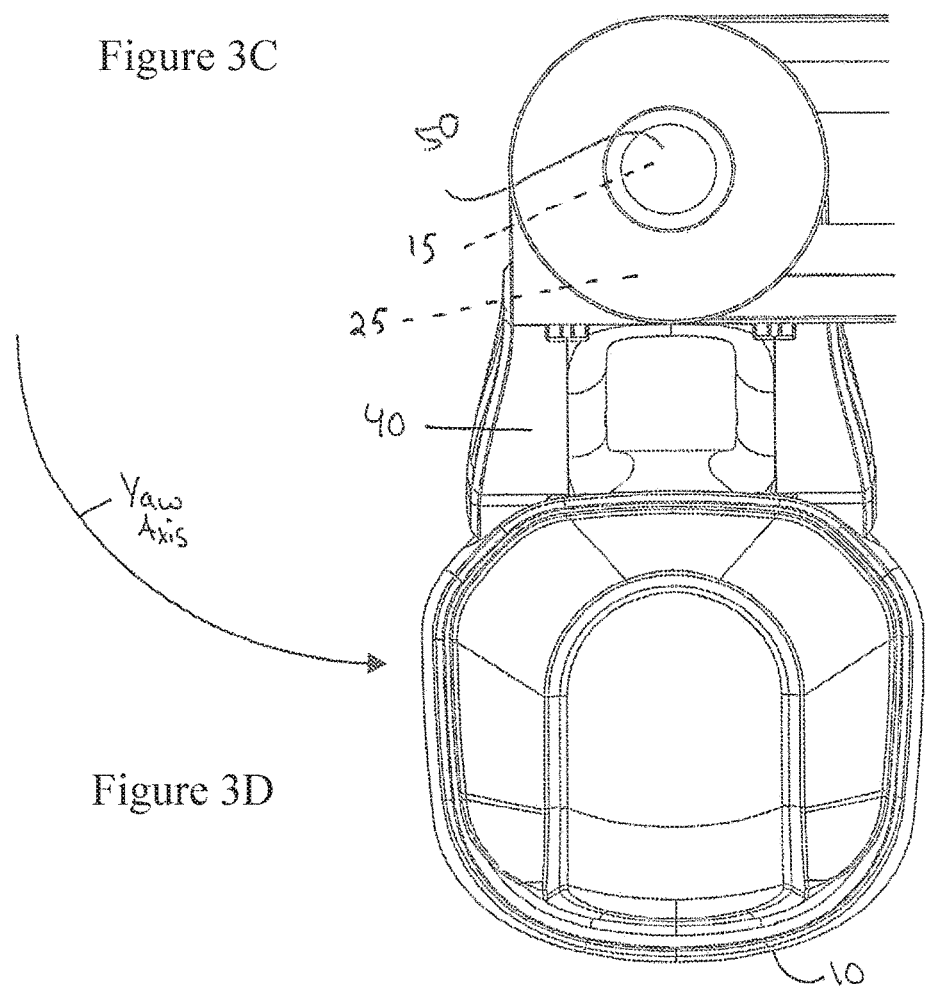
Figure 3E:
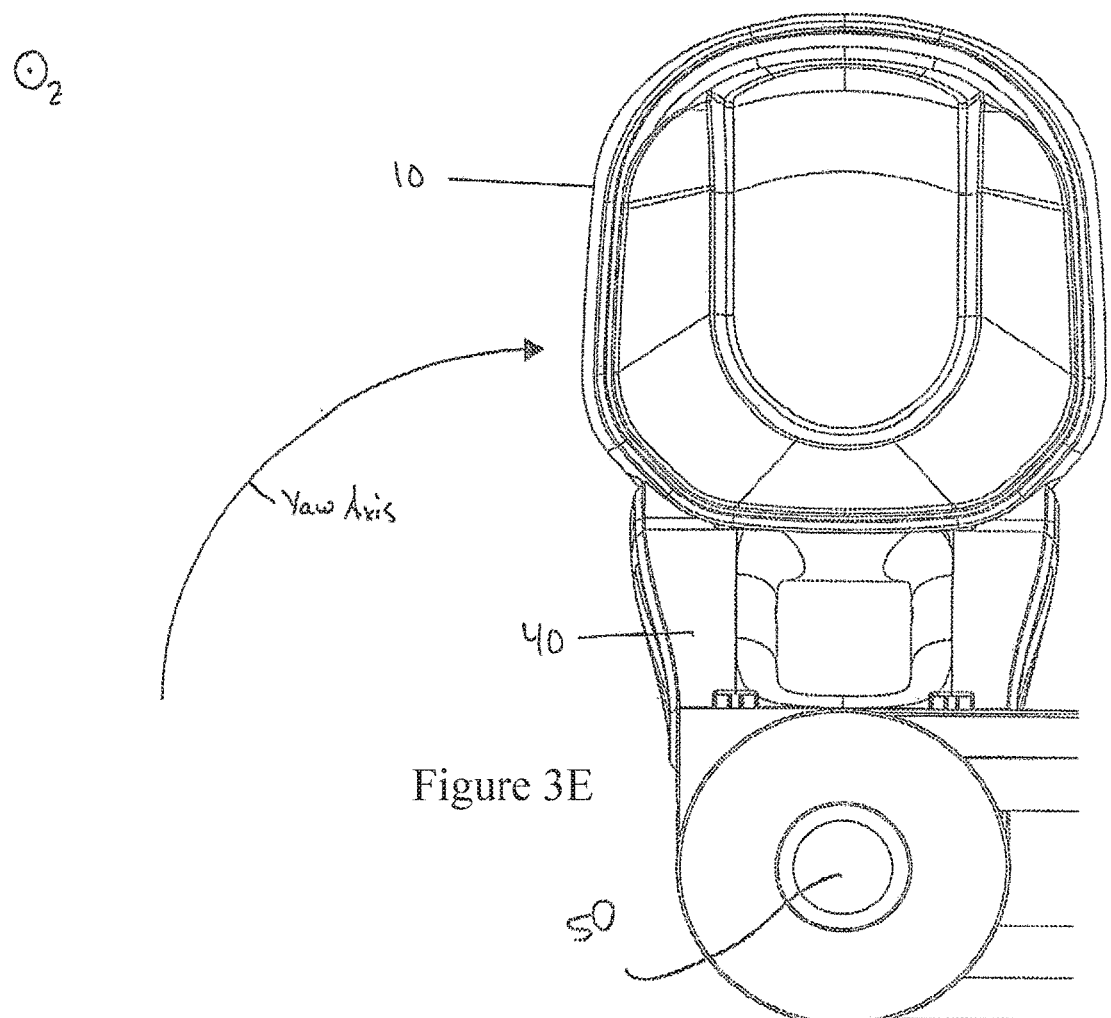
Figure 3F:
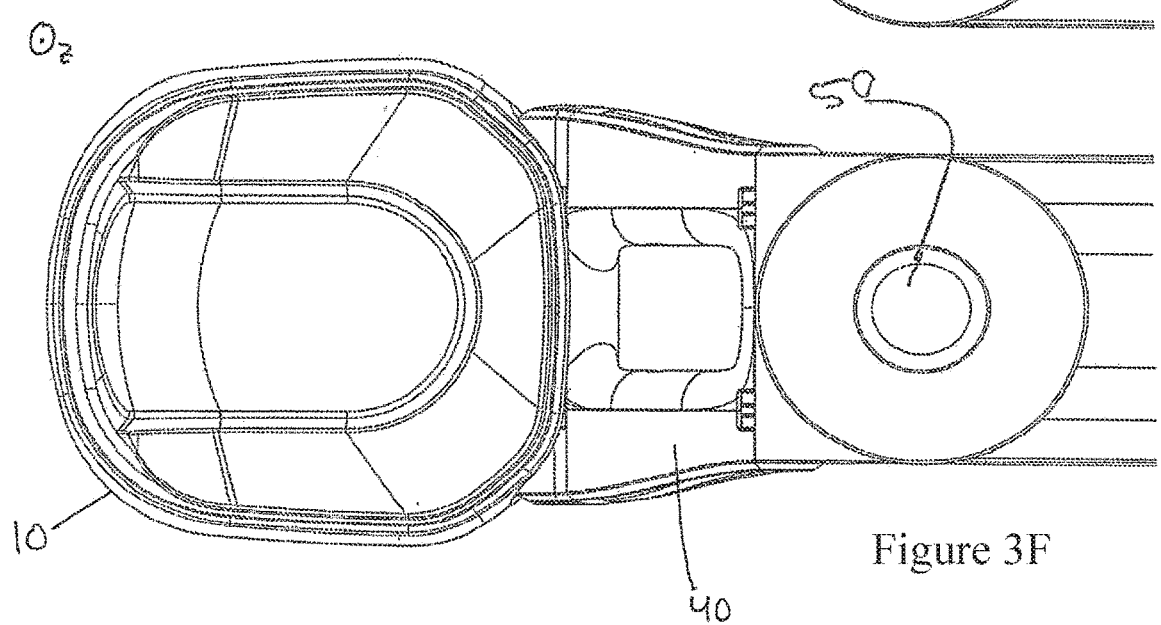
Figure 4A:
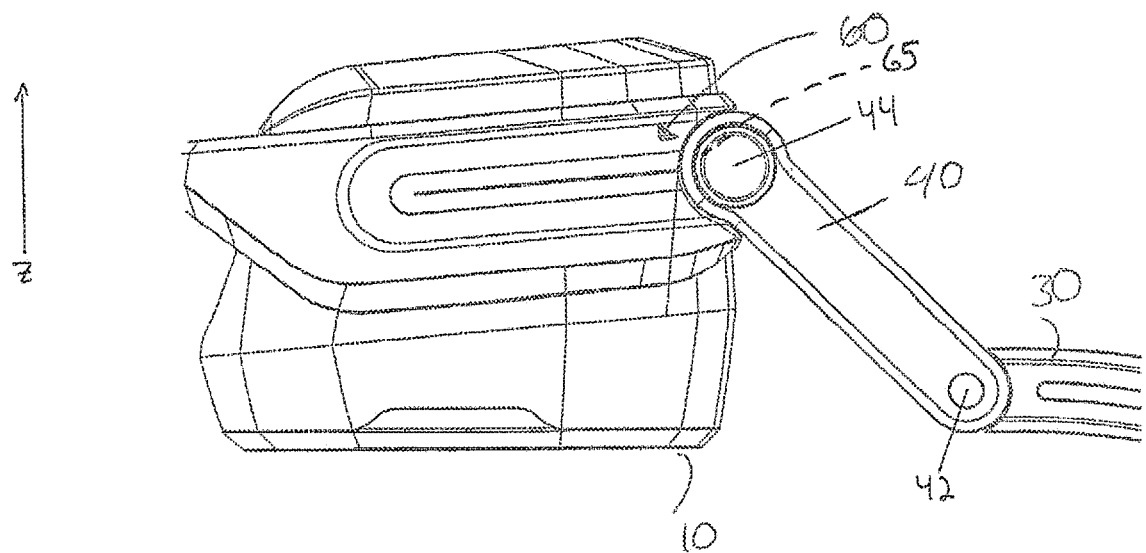
FIGS. 4A-4F illustrate an embodiment of the C-arm fluoroscope system with a curved track that joins an imaging head to the C-arm to allow the imaging head to be rotated in accordance with the disclosed technology.
Figure 4B:
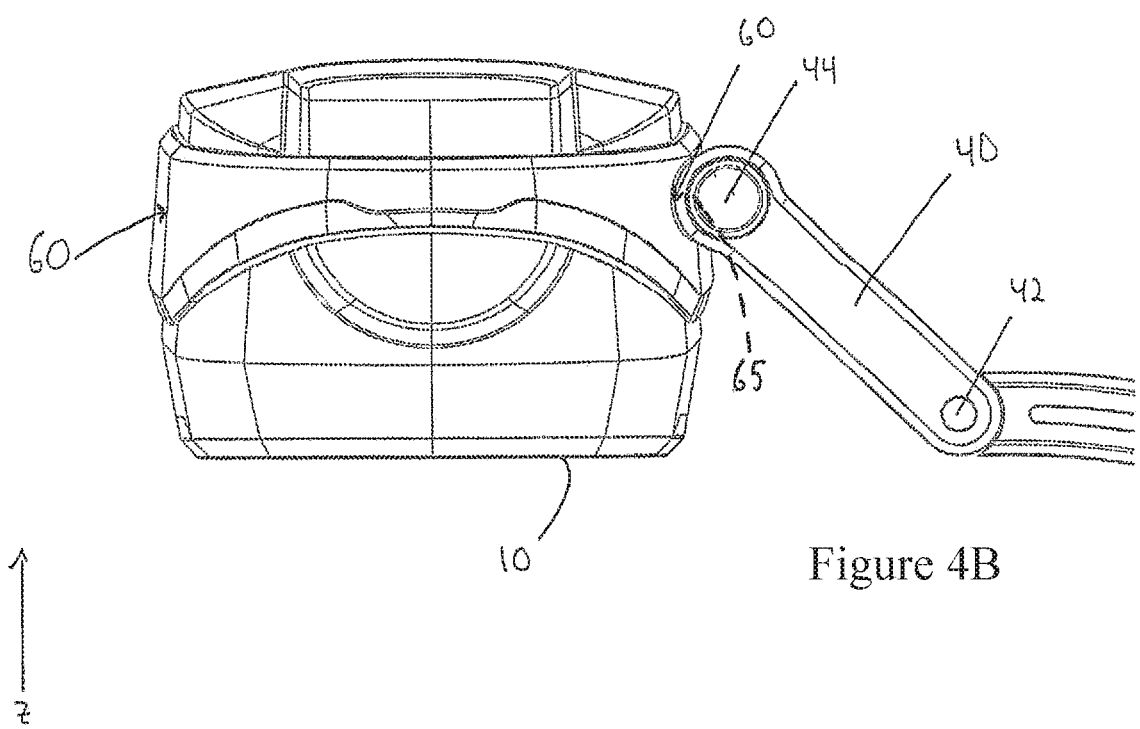
Figure 4C:
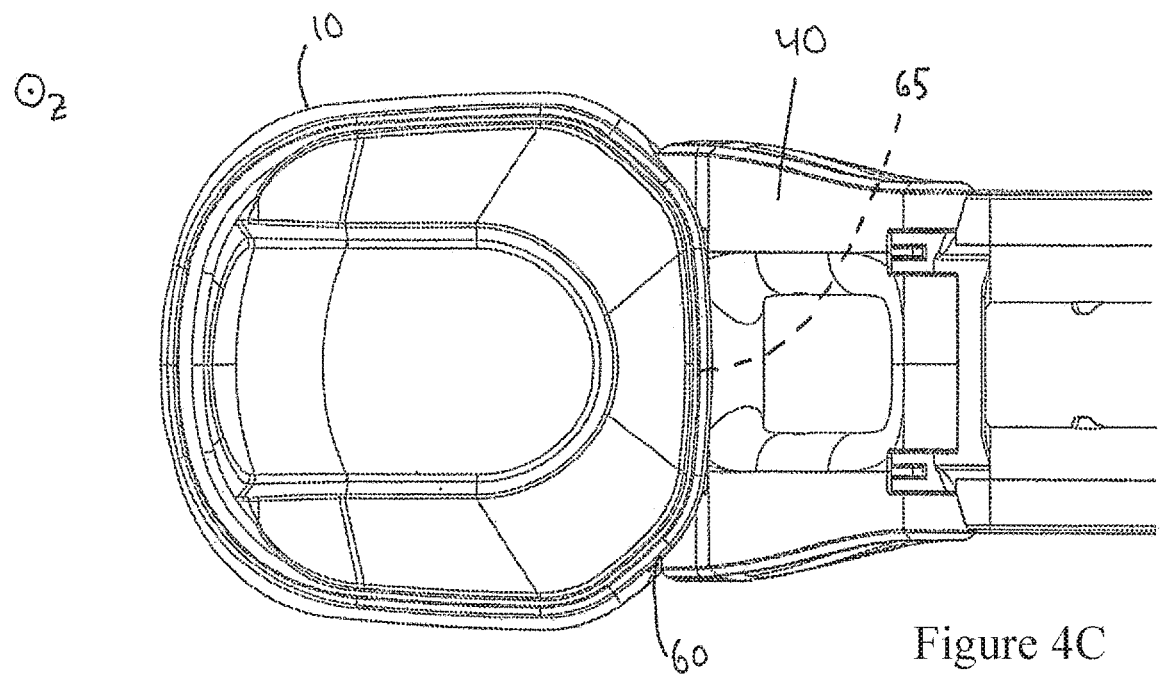
Figure 4D:
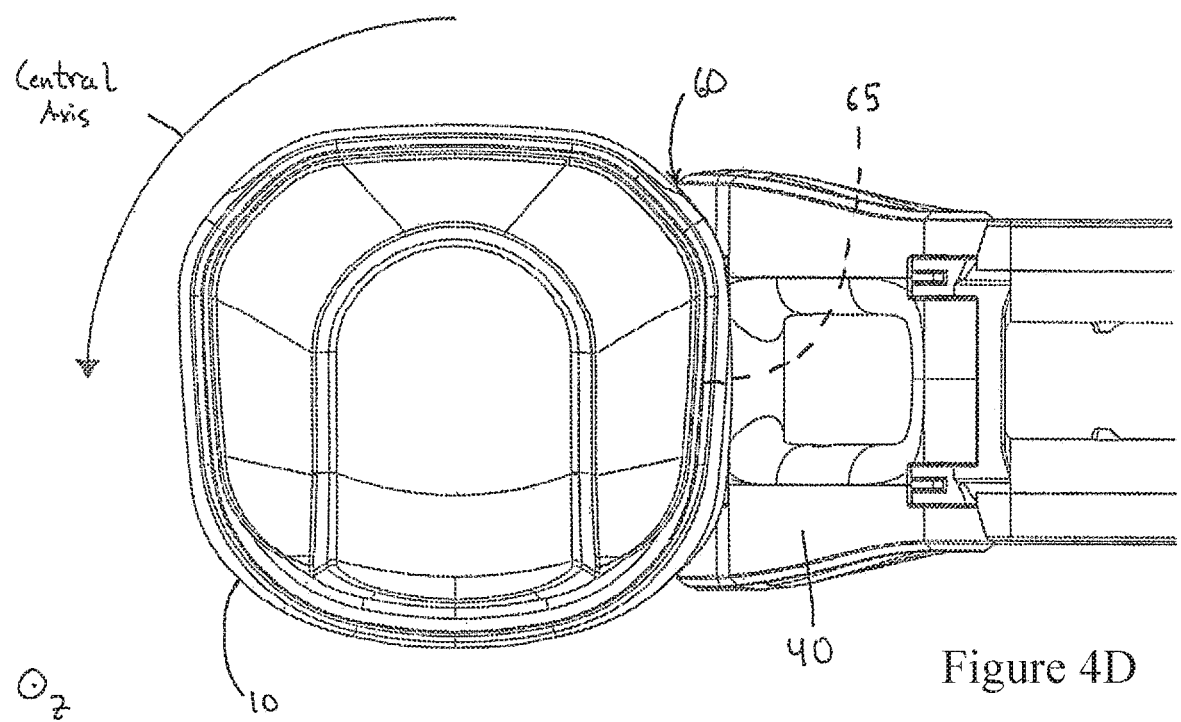
Figure 4E:
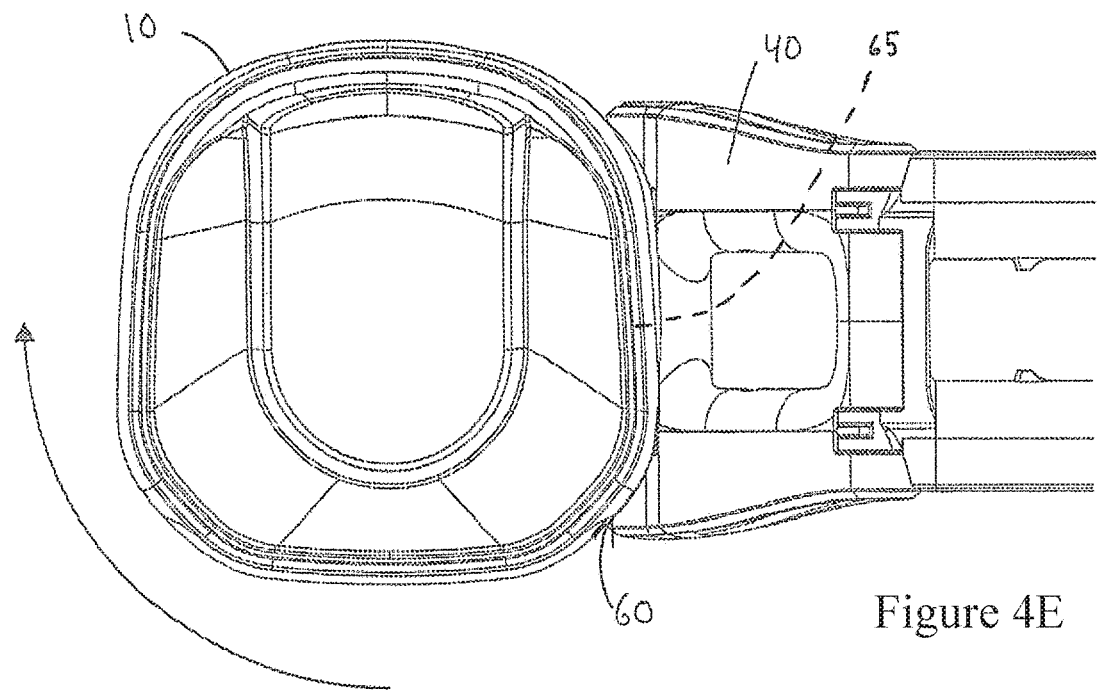
Figure 4F:
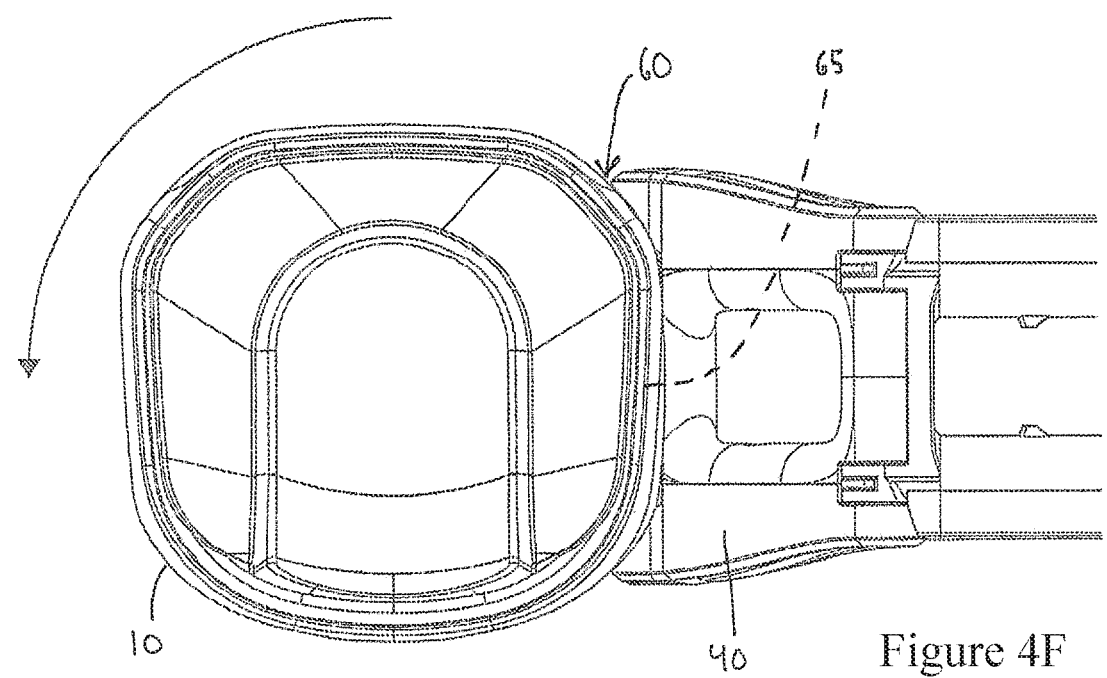
Figure 5A:
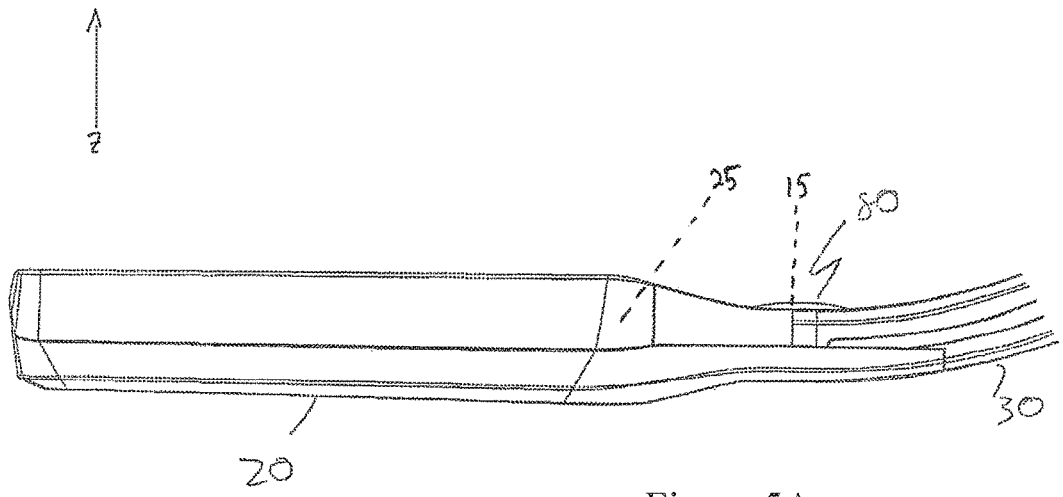
FIGS. 5A-5F illustrate the C-arm fluoroscope system with an X-ray detector mounted to the C-arm with a hinge that allows the X-ray detector to be rotated left/right in accordance with the disclosed technology.
Figure 5B:
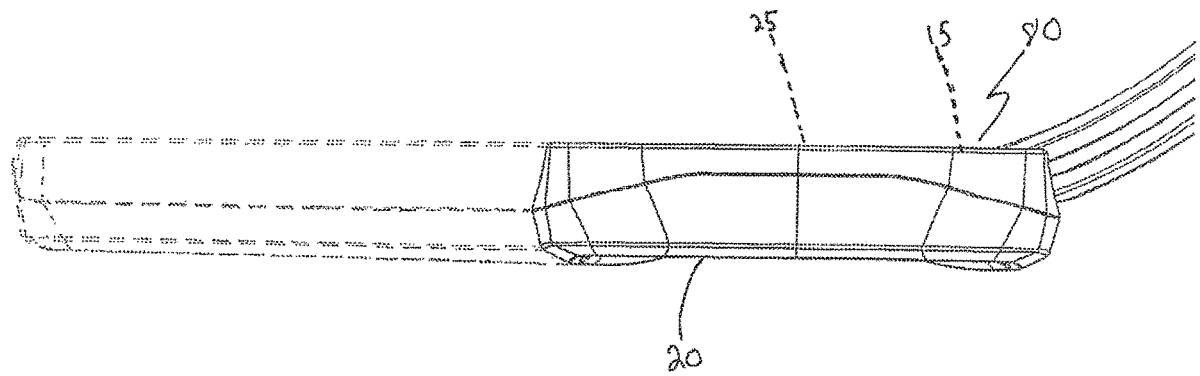
Figure 5C:
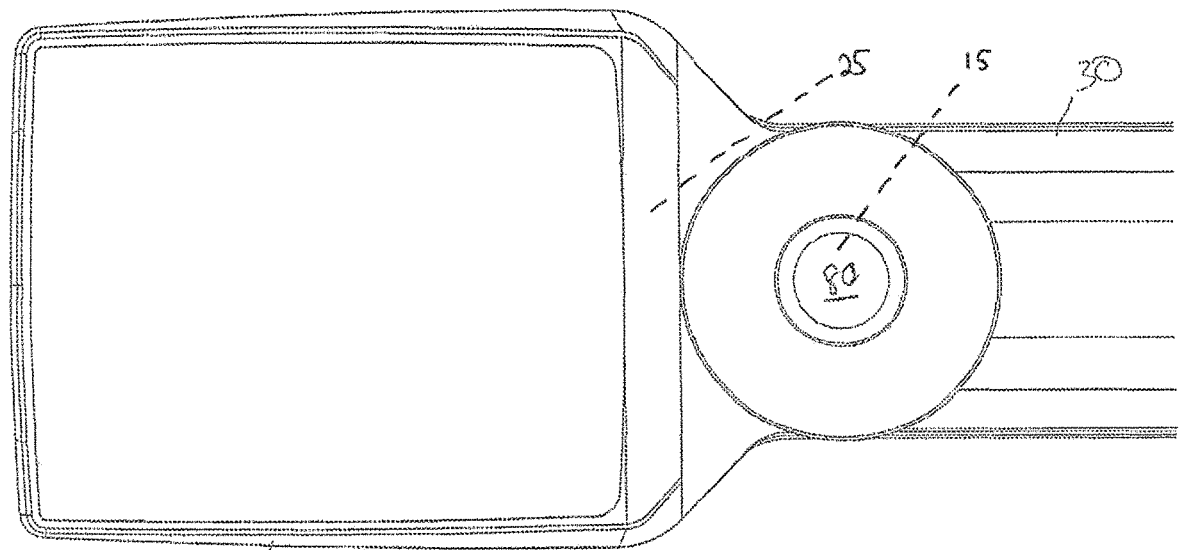
Figure 5D:
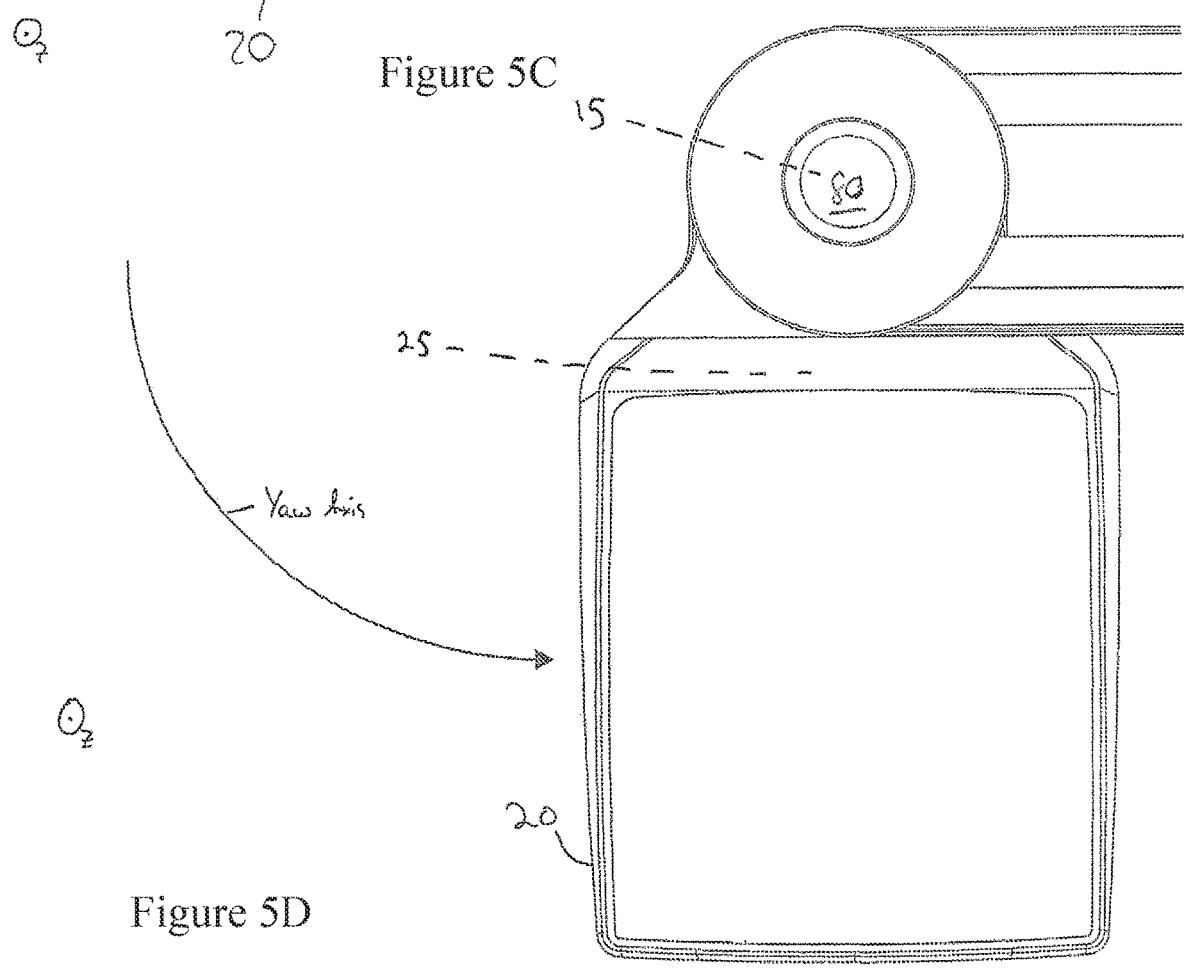
Figure 5E:
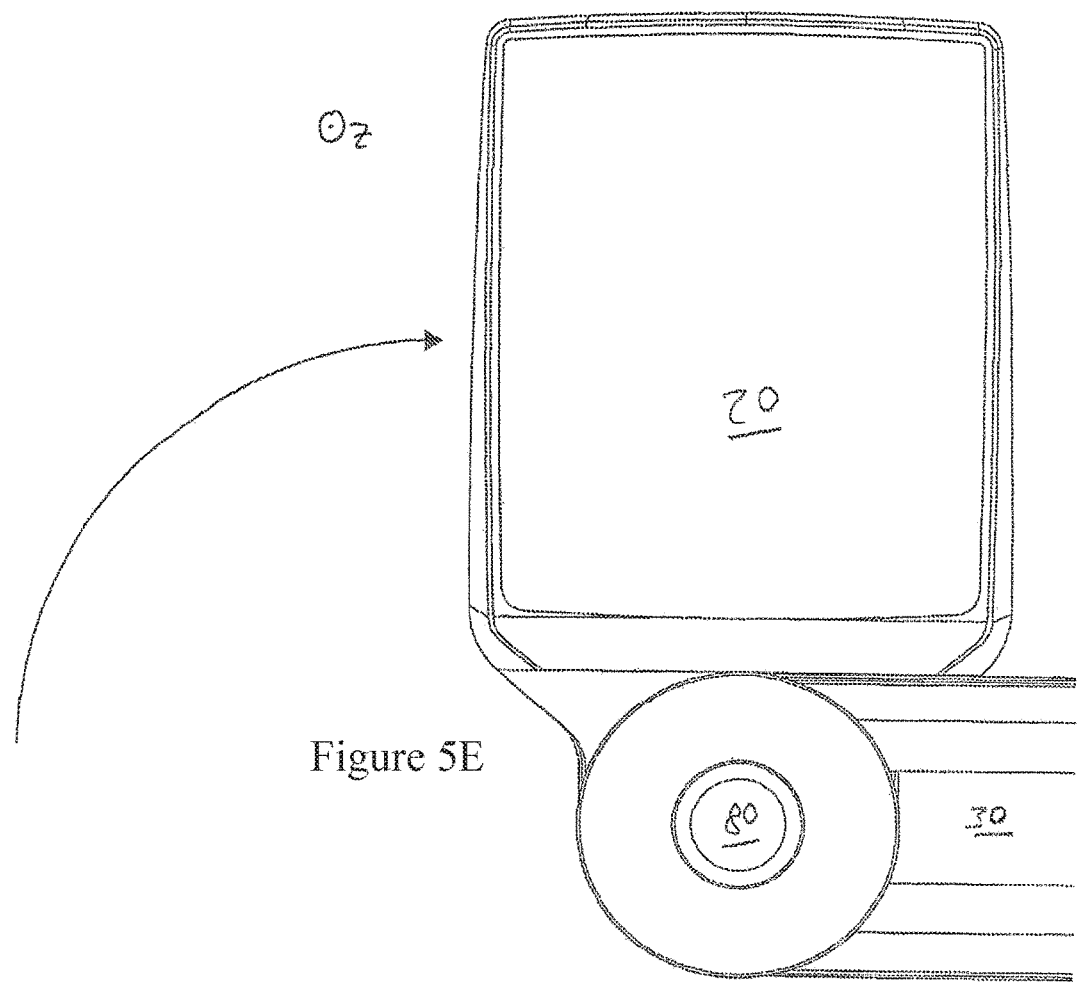
Figure 5F:
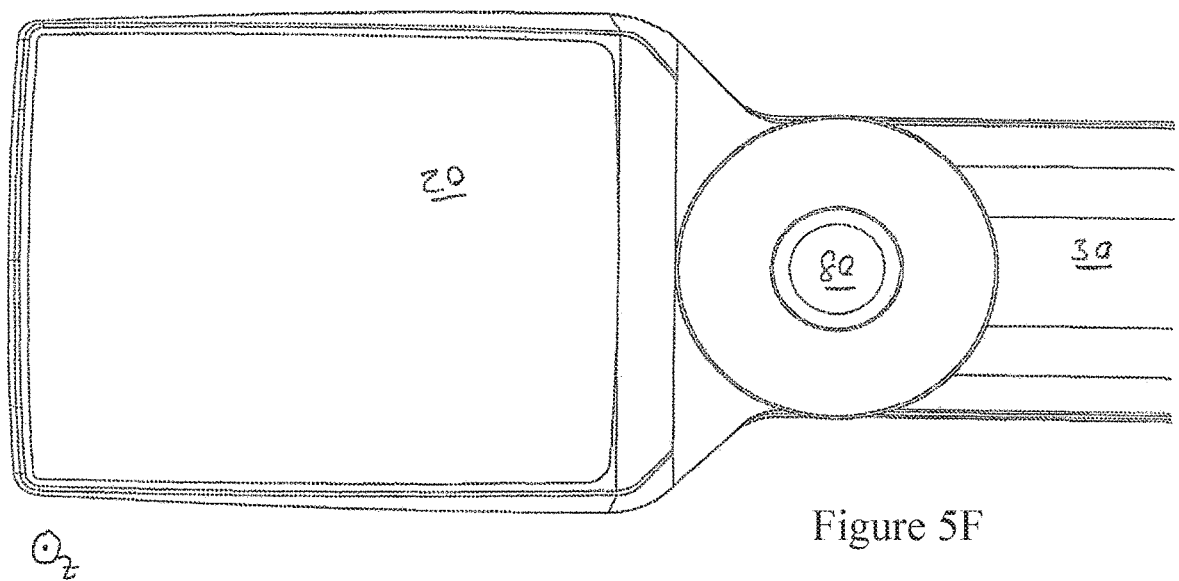
Figure 6A:
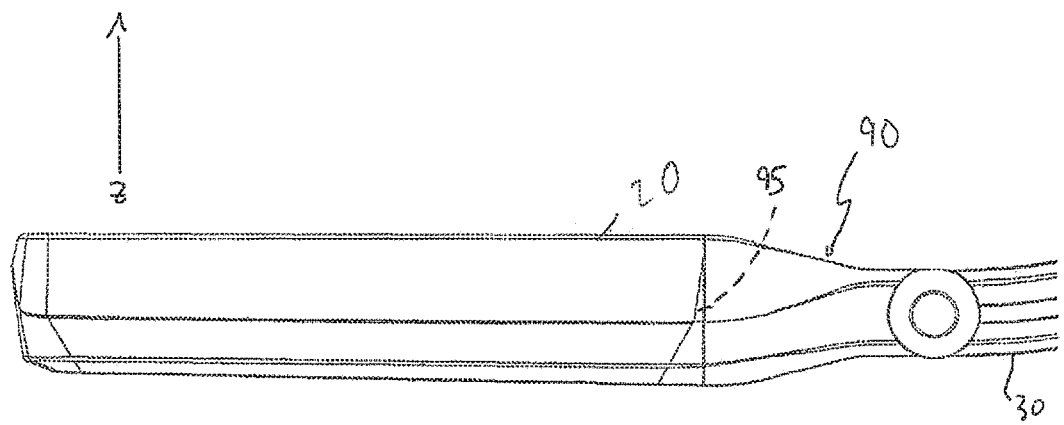
FIGS. 6A-6F illustrate an embodiment of the C-arm fluoroscope system with a curved track that joins an X-ray detector to the C-arm to allow the detector to be rotated left/right in accordance with the disclosed technology.
Figure 6B:
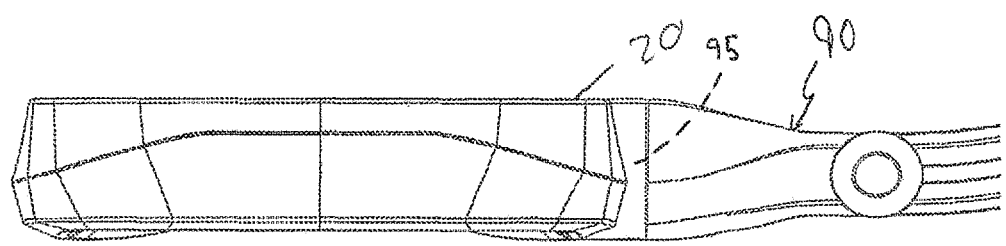
Figure 6C:
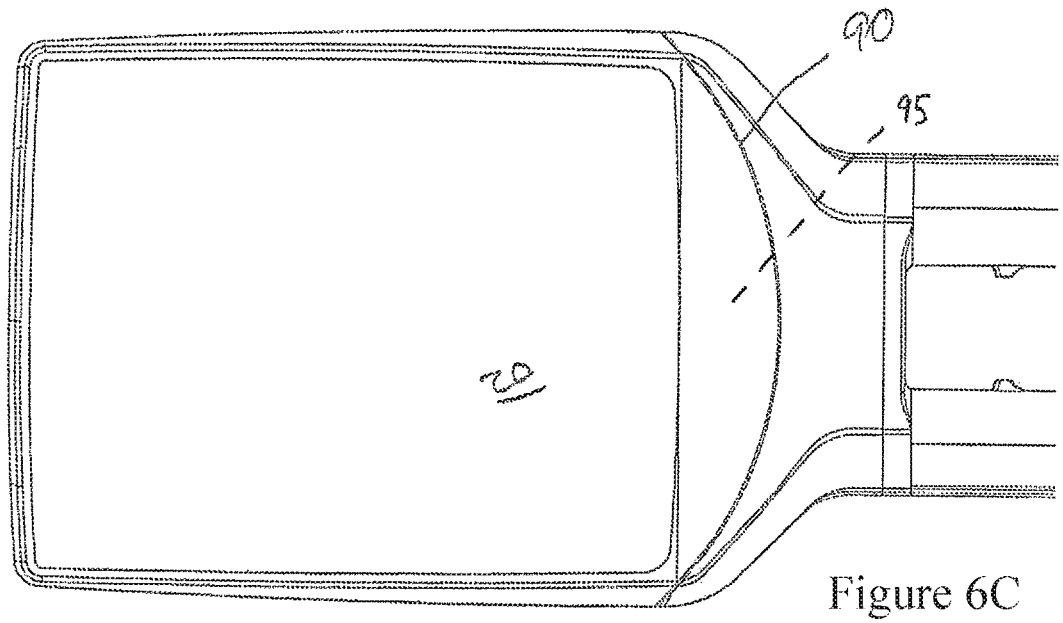
Figure 6D:
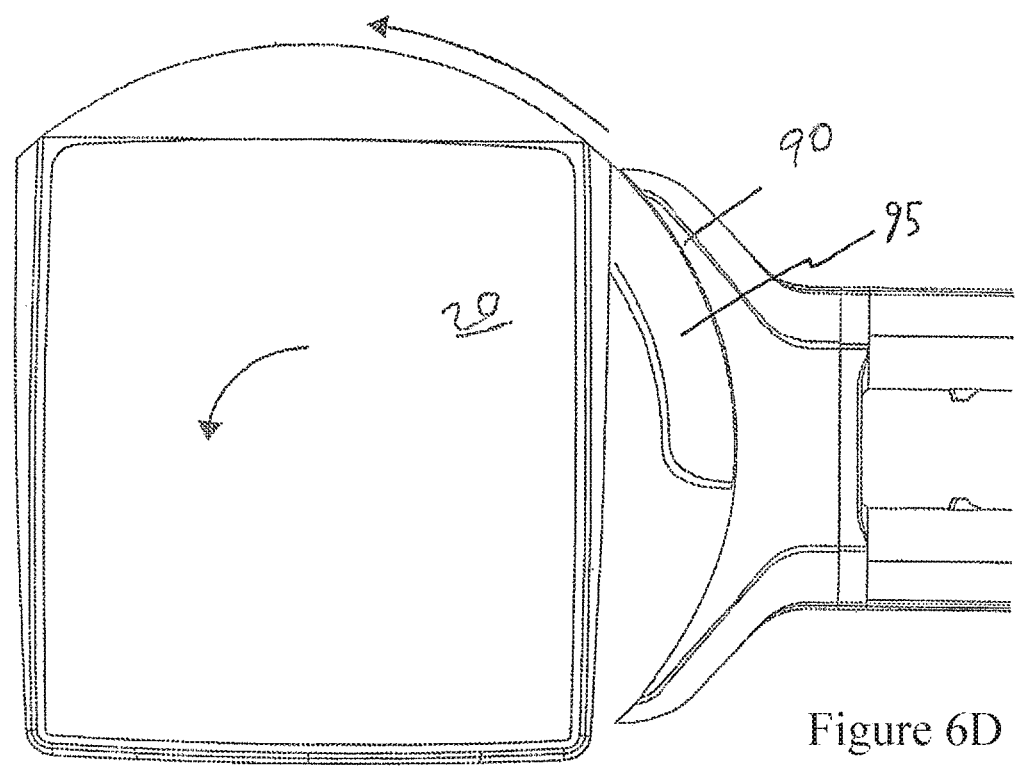
Figure 6E:
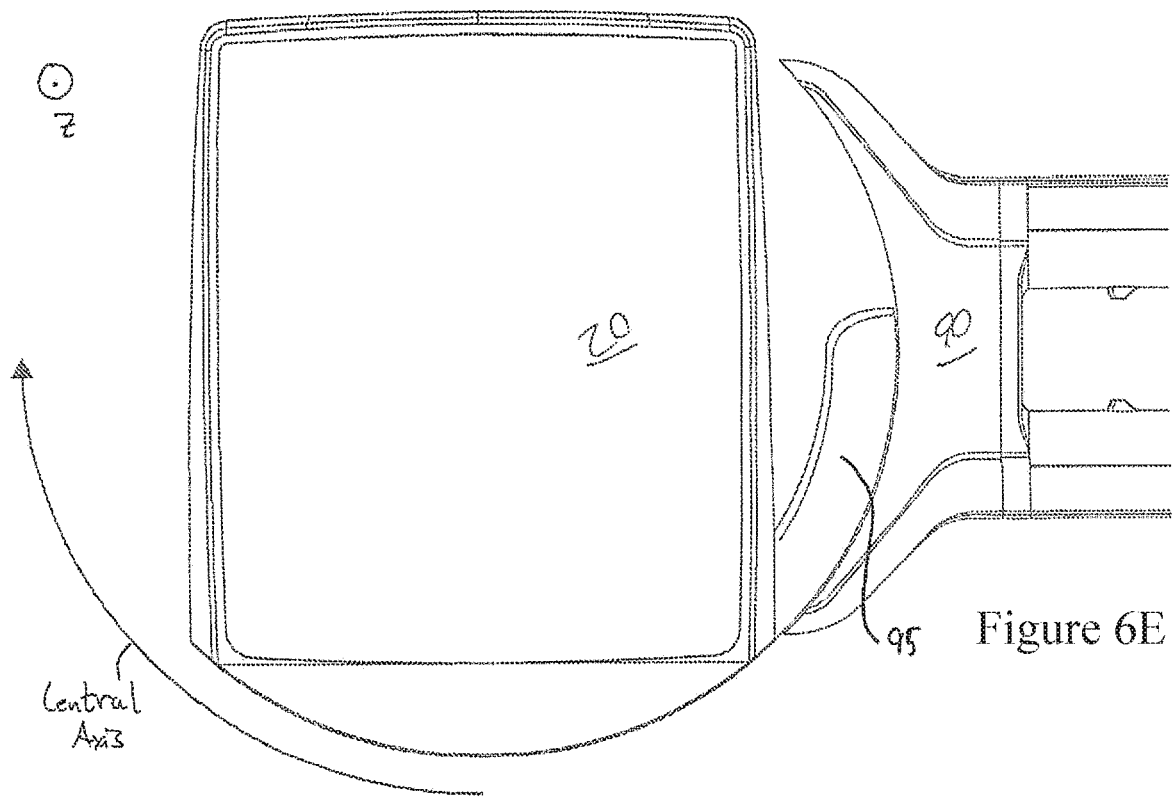
Figure 6F:
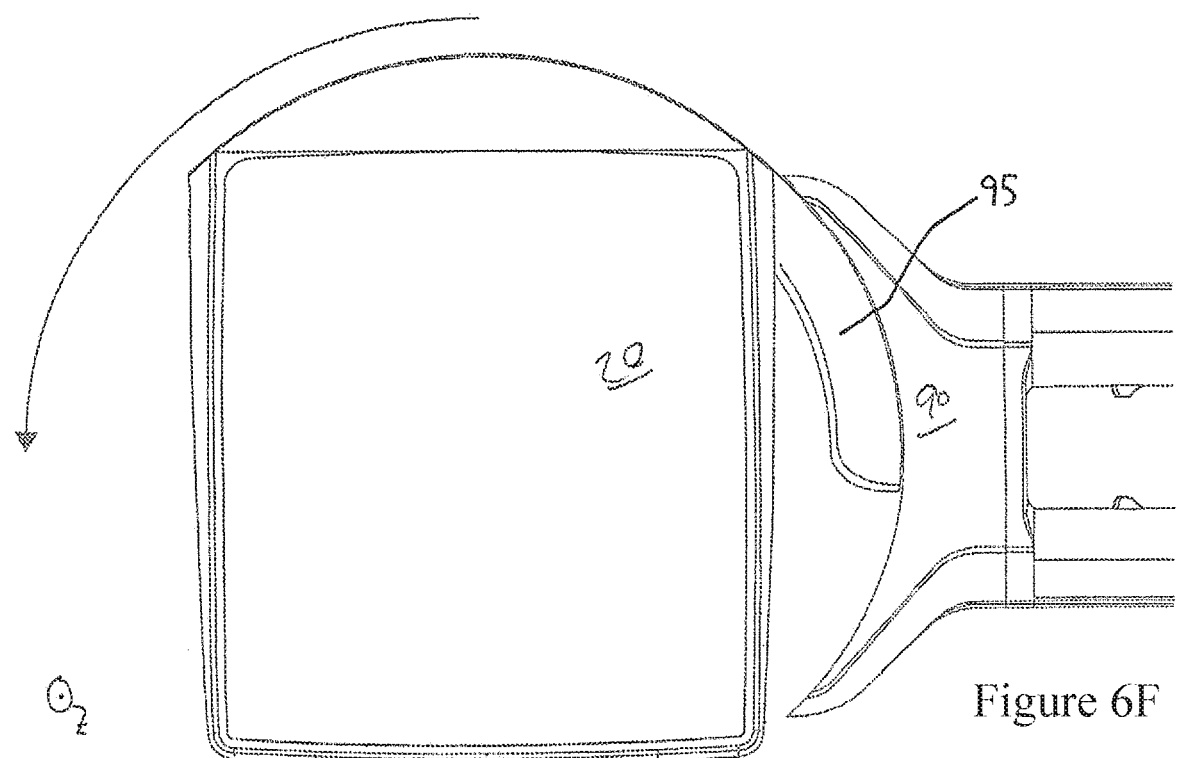

However, as illustrated in FIGS. 2C-2E, the vertical hinge mechanism 40 can also allow the imaging head 10 to be rotated (e.g., further tilted up) away from the X-ray detector 20 via a second, independently movable joint 44, providing the imaging head 10 with more freedom to be moved out of the way. In this orientation, the X-ray imaging head 10 can be moved and positioned such that it is not pointed towards nor aligned with the X-ray detector 20. For example, the position illustrated in FIG. 2E can be used to give the physician or X-ray technician more room to position the subject, more room to use an instrument on a subject, etc., without needing to move the fluoroscope or subject entirely. In some embodiments, the vertical hinge mechanism 40 is designed to always allow the additional movement away from the X-ray detector 20. In other embodiments, a lock 45 on the vertical hinge mechanism 40 prevents the additional movement until it is undone or removed by an operator.

When the imaging head 10 is oriented away from the X-ray detector 20 such that the imaging components 10, 20 are mis-aligned, switches 15 and/or position sensors 25 (mechanical, optical, acoustic, infrared, accelerometers, or the like) detect the mis-alignment and produce signals that are communicated to and read by the controlling computer system 35 (FIG. 1) to prevent the generation of X-rays when the imaging head is not pointed towards the X-ray detector, or to alert a physician or technician of the mis-alignment to reduce likelihood of unintended exposure. In another embodiment, the switches 15 and/or position sensors 25 can be configured to provide a signal only when the X-ray detector 20 and the imaging head 10 are properly aligned relative to each other for purposes of generating X-ray images.

In the embodiments shown in FIGS. 3A-3F, the imaging system includes a horizontal hinge 50 that joins the imaging head 10 to the C-arm 30, such that the imaging head 10 can be rotated left and right (e.g., along a yaw axis) away from alignment with the X-ray detector 20. A physician or X-ray technician can swing the imaging head 10 in a direction substantially perpendicular the supporting C-arm 30 to provide additional room for positioning a subject or using an instrument (not shown). As further illustrated in FIGS. 3A-3F, the horizontal hinge 50 can be positioned between the vertical hinge mechanism 40 and the C-arm 30, allowing for a combination of the freedoms offered by the vertical hinge mechanism 40 and the horizontal hinge 50 (e.g., allowing both vertical movement and movement along the yaw axis).

FIGS. 4A-4F illustrate an embodiment where the imaging head 10 is secured to the C-arm 30 with mounting elements 65 slidably engaging a curved track 60 (for example, via ball joints and a curved socket) surrounding an exterior of the imaging head 10. The curved track 60 allows the imaging head 10 to be rotated about a center axis of the imaging head 10, shown by the lines indicating the central axis. In this embodiment, movement of the imaging head 10 can be substantially parallel to the X-ray detector 20, but rotationally out of alignment with the X-Ray detector 20, such that the imaging head 10 would not be properly positioned for obtaining X-ray images.

In some embodiments, the relative position of the imaging head 10 and the X-ray detector 20 can change by moving the imaging head 10 relative to the C-arm 30. In other embodiments, the relative position of the imaging head 10 and X-ray detector 20 can be changed by moving the X-ray detector 20 relative to the C-arm 30. For example, FIGS. 5A-5F show an embodiment where the X-ray detector 20 is secured to the C-arm 30 with a hinge mechanism, referred to as a horizontal hinge 80, that allows the X-ray detector 20 to move left and right from the C-arm 30 (e.g., along the yaw-axis in FIG. 5D). In some embodiments, the hinge 80 includes switches 15 or other sensors 25 to produce signals that inform a controlling computer system of the position of the X-ray detector 20 so that the computer system 35 (FIG. 1) can prevent the generation of X-rays if the imaging head 10 is not substantially aligned with the X-ray detector 20.

FIGS. 6A-6F show an embodiment where the X-ray detector 20 is secured to the C-arm 30 with a mounting element 95 slidably engaging a curved track 90 (for example, via ball joints and curved sockets) to allow the X-ray detector 20 to be rotated around its center point with respect to the C-arm 30, shown by the central axis. In this embodiment, movement of the X-ray detector 20 can be substantially parallel to the imaging head 10, but rotationally out of alignment with the imaging head 10, such that the X-ray detector 20 would not be properly positioned for obtaining X-ray images.

FIGS. 7A-7C illustrate an embodiment where the X-ray detector 20 is mounted to the C-arm 30 with a hinge mechanism, referred to as a vertical hinge 100, that allows the X-ray detector 20 to be tilted up and down with respect to the imaging head 10 and the C-arm 30. As further illustrated in FIGS. 7A-7C, the vertical hinge 100 can be operably connected to the curved track 90. In this embodiment, the X-ray detector 20 is provided with the freedom to tilt both up and down along the Z-axis and rotate about the central axis. Further, the horizontal hinge 80 can also be incorporated into the adjoining region of the X-ray detector 20 and the C-arm 30, providing the X-ray detector 20 with three distinct axes of motion with respect to the imaging head 10 and C-arm 30. In other embodiments, a lock 75 on the vertical hinge 100 prevents the additional movement until it is undone or removed by an operator.

The various embodiments of fluoroscope system can all include switches 15 and/or sensors 25 (see FIGS. 2A-2D, 3A-3D, and 5A-5D) that detect a mis-alignment between the imaging head 10 and X-ray detector 20. The switches 15 and/or sensors 25 can produce signals that are communicated to and read by a controlling computer system 35 (FIG. 1). Software, e.g., computer-executable instructions stored on one or more computer-readable storage mediums, is executed by a processor of the computer system 35 to read the signals from the sensors and either prevent the X-ray source from firing or alert the operator of the mis-alignment and/or of proper alignment. The operator can then be required to confirm the orientation of the imaging head 10 or X-ray detector 20 before the computer system will fire the X-ray.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions encoded on computer storage medium for execution by, or to control the operation of, data processing apparatus.

A computer-readable storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

To provide for interaction with an operator of the fluoroscope, embodiments of the subject matter described in this specification can be implemented on a computer having a display device, e.g., an LCD (liquid crystal display), LED (light emitting diode), or OLED (organic light emitting diode) monitor, for displaying information to the user, and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback, and input from the user can be received in any form, including acoustic, speech, or tactile input. In addition, a computer can interact with a user by sending documents to and receiving documents from a device that is used by the user, for example, by sending web pages to a web browser on a user's client device in response to requests received from the web browser.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A fluoroscope assembly, comprising:
a contoured support arm having opposing first and second end portions;
an adjustment element coupled to the first end portion;
an imaging head coupled to the adjustment element, wherein the adjustment element is movable to adjust a position of the imaging head relative to the first and second end portions; and
an X-ray detector coupled to the second end portion;
wherein the adjustment element comprises a track coupled to the imaging head and a mounting element adjoining the track to the support arm, and wherein the track and mounting element are configured to allow the imaging head to rotate about a center axis of the imaging head; and
wherein the adjustment element is configured to allow the imaging head to be moved between an aligned position with the imaging head aligned with the X-ray detector for generating an X-ray image, and a misaligned position wherein the imaging head is not substantially aligned with the X-ray detector.

2. The fluoroscope assembly of claim 1 wherein the adjustment element comprises a first hinging mechanism comprising:
an arm portion;
a first hinge coupling the arm portion to the first end portion of the support arm and allowing the imaging head to be moved about the first hinge toward or away from the X-ray detector; and
a second hinge coupling the arm portion to the imaging head and allowing the imaging head to be rotated about the second hinge toward or away from the X-ray detector, wherein movement about the second hinge is substantially independent from movement about the first hinge.

3. The fluoroscope assembly of claim 1 wherein the adjustment element comprises a hinging mechanism configured to allow the imaging head to be rotated on a yaw axis along a plane substantially parallel to the X-ray detector.

4. A fluoroscope assembly, comprising:
a contoured support arm having opposing first and second end portions;
an adjustment element coupled to the first end portion;
an imaging head coupled to the adjustment element, wherein the adjustment element is movable to adjust a position of the imaging head relative to the first and second end portions; and
an X-ray detector coupled to the second end portion;
wherein the adjustment element comprises:
a first hinging mechanism coupled to the support arm and configured to allow the imaging head to be rotated on a yaw axis for movement in a first plane toward or away from the X-ray detector;
a second hinge mechanism having:
an arm portion;
a first hinge connecting the arm portion to the first hinging mechanism and allowing the imaging head to be raised or lowered with respect to the X-ray detector;
an independently addressable second hinge coupled to the arm portion and allowing the imaging head to be rotated in a second plane orthogonal to the first plane for movement away from or towards the X-ray detector; and
a mounting element coupled to the imaging head; and
a shaped track coupled to the imaging head and configured to engage with the mounting element, wherein the shaped track and mounting element are configured to allow the imaging head to rotate about a center axis of the imaging head; and
wherein the adjustment element is configured to allow the imaging head to be moved between an aligned position with the imaging head aligned with the X-ray detector for generating an X-ray image, and a misaligned position wherein the imaging head is not substantially aligned with the X-ray detector.

5. The fluoroscope assembly of claim 1 wherein the contoured support arm is an arcuate support arm.

6. The fluoroscope assembly of claim 1 wherein the contoured support arm is a C-shaped support arm.

7. The fluoroscope assembly of claim 1 wherein the adjustment element comprises a vertical hinging mechanism coupled between the first end portion of the support arm and the imaging head, the vertical hinging mechanism configured to allow the imaging head to be rotated about one or more axes away from or towards the X-ray detector.

8. The fluoroscope assembly of claim 1 wherein the adjustment element comprises a horizontal hinging mechanism configured to allow the imaging head to be rotated on a yaw axis away from the X-ray detector for movement in a plane substantially parallel to the X-ray detector.

9. The fluoroscope assembly of claim 1, further comprising:
a switch having an unlocked state and a locked state, wherein the switch is configured to prevent power to the imaging head when in the locked state;
at least one sensor to detect a mis-aligned status when the imaging head is not substantially aligned with the X-ray detector and send a communication of the misaligned status;
a processor; and
one or more computer-readable storage mediums for storing computer-executable instructions configured to cause the processor to:
receive the communication; and
move the switch into the locked state.

10. A fluoroscope assembly, comprising:
a shaped support arm having a first distal end portion and a second distal end portion;
an adjustment element operably connected to the first distal end portion;
an imaging head operably connected to the adjustment element; and
an X-ray detector operably connected to the second distal end portion;
wherein the adjustment element comprises a track attached to the imaging head and a mounting element adjoining the track to the support arm, and wherein the track and mounting element are configured to allow the imaging head to rotate about a center axis of the imaging head; and
wherein the adjustment element is configured to allow the imaging head to be moved such that the imaging head is not substantially aligned with the X-ray detector.

11. The fluoroscope assembly of claim 10 wherein the adjustment element comprises a vertical hinge mechanism having:
an arm portion;
a first hinge connecting the arm portion to the support arm and allowing the imaging head to be raised or lowered with respect to the X-ray detector; and an independently addressable second hinge connecting the arm portion to the imaging head and allowing the imaging head to be rotated away from or towards the X-ray detector.

12. The fluoroscope assembly of claim 10 wherein the adjustment element comprises a horizontal hinge configured to allow the imaging head to be rotated on a yaw axis away from the X-ray detector.

13. A fluoroscope assembly comprising:
a shaped support arm having a first distal end portion and a second distal end portion;
an adjustment element operably connected to the first distal end portion,
an imaging head operably connected to the adjustment element; and
an X-ray detector operably connected to the second distal end portion;
wherein the adjustment element comprises:
  a horizontal hinge connected to the support arm and configured to allow the imaging head to be rotated on a yaw axis away from the X-ray detector;
  a vertical hinge mechanism having:
    an arm portion;
    a first hinge connecting arm portion to the horizontal hinge and allowing the imaging head to be raised or lowered with respect to the X-ray detector;
    an independently addressable second hinge connected to the arm portion and allowing the imaging head to be rotated away from or towards the X-ray detector; and
    a mounting element for engaging the imaging head; and
  a curved track attached to an outside wall of the imaging head and configured to engage with the mounting element, wherein the curved track and mounting element are configured to allow the imaging head to rotate about a center axis of the imaging head; and
wherein the adjustment element is configured to allow the imaging head to be moved such that the imaging head is not substantially aligned with the X-ray detector.

14. A fluoroscope assembly, comprising:
a support arm having a first distal end portion and a second distal end portion;
a first adjustment element coupled to the first distal end portion;
an imaging head movably coupled to the first adjustment element;
a second adjustment element coupled to the second distal end; and
an X-ray detector movably coupled to the second adjustment element;
wherein the first adjustment element comprises:
  a horizontal hinge connected to the support arm and configured to allow the imaging head to be rotated on a yaw axis away from the X-ray detector:
  a vertical hinge mechanism having:
    an arm portion:
    a first hinge connecting arm portion to the horizontal hinge and allowing the imaging head to be raised or lowered with respect to the X-ray detector;
    an independently addressable second hinge connected to the arm portion and allowing the imaging head to be rotated away from or towards the X-ray detector; and
    a mounting element for engaging the imaging head; and
  a track attached to an outside wall of the imaging head and configured to engage with the mounting element, wherein the track and mounting element are configured to allow the imaging head to rotate about a center axis of the imaging head;
wherein the first adjustment element is configured to allow the imaging head to be moved relative to the support arm between a first aligned position with the imaging head in alignment with the X-ray detector for generating X-ray images, and a first misaligned position with the imaging head out of alignment with the X-ray detector not suitable for generating X-ray images; and
wherein the second adjustment element is configured to allow the X-ray detector to be moved relative to the support arm between a second aligned position with the X-ray detector in alignment with the imaging head for generating X-ray images, and a second misaligned position with the X-ray detector out of alignment with the imaging head not suitable for generating X-ray images.

15. The fluoroscope assembly of claim 14, further comprising:
a first locking element operably coupled to the first adjustment element and configured to prevent movement in the first adjustment element and imaging head relative to the X-ray detector until unlocked; and
a second locking element operably coupled to the second adjustment element and configured to prevent movement in the second adjustment element and X-ray detector relative to the imaging head until unlocked.

16. The fluoroscope assembly of claim 14, further comprising:
a switch having an unlocked state and a locked state, wherein the switch is configured to prevent power to the imaging head when in the locked state;
at least one sensor to detect a mis-aligned status when the imaging head is not substantially aligned with the X-ray detector and send a communication of the mis-aligned status;
a processor; and
one or more computer-readable storage mediums for storing computer-executable instructions configured to cause the processor to:
  receive the communication; and
  move the switch into the locked state.

17. A fluoroscope assembly, comprising:
a support arm having a first distal end portion and a second distal end portion;
a first adjustment element coupled to the first distal end portion;
an imaging head movably coupled to the first adjustment element;
a second adjustment element coupled to the second distal end; and
an X-ray detector movably coupled to the second adjustment element;
wherein the second adjustment element comprises:
  a horizontal hinge connected to the support arm and configured to allow the X-ray detector to be rotated on a yaw axis away from the imaging head;
  a vertical hinge, wherein the vertical hinge allows the X-ray detector to be rotated away from or towards the imaging head; and a curved track attached to an outside wall of the X-ray detector and a mounting element adjoining the track to the vertical hinge, wherein the curved track and mounting element are configured to allow the X-ray detector to rotate about a center axis of the X-ray detector;

wherein the first adjustment element is configured to allow the imaging head to be moved relative to the support arm between a first aligned position with the imaging head in alignment with the X-ray detector for generating X-ray images, and a first misaligned position with the imaging head out of alignment with the X-ray detector not suitable for generating X-ray images; and wherein the second adjustment element is configured to allow the X-ray detector to be moved relative to the support arm between a second aligned position with the X-ray detector in alignment with the imaging head for generating X-ray images, and a second misaligned position with the X-ray detector out of alignment with the imaging head not suitable for generating X-ray images.

\* \* \* \* \*